United States Patent
Talebpour et al.

(10) Patent No.: US 10,988,794 B2
(45) Date of Patent: *Apr. 27, 2021

(54) METHODS OF TARGETED ANTIBIOTIC SUSCEPTIBILITY TESTING

(71) Applicant: Qvella Corporation, Richmond Hill (CA)

(72) Inventors: Samad Talebpour, Richmond Hill (CA); Aye Aye Khine, Thornhill (CA); Tino Alavie, Thornhill (CA); Stephen Wesley Leonard, Unionville (CA)

(73) Assignee: QVELLA CORPORATION, Richmond Hill (CA)

( * ) Notice: Subject to any disclaimer, the term of this patent is extended or adjusted under 35 U.S.C. 154(b) by 106 days.

This patent is subject to a terminal disclaimer.

(21) Appl. No.: 16/280,842

(22) Filed: Feb. 20, 2019

(65) Prior Publication Data

US 2019/0177766 A1    Jun. 13, 2019

Related U.S. Application Data

(63) Continuation of application No. 14/901,200, filed as application No. PCT/CA2014/050634 on Jul. 3, 2014, now Pat. No. 10,233,483.

(60) Provisional application No. 61/842,827, filed on Jul. 3, 2013.

(51) Int. Cl.
    *C12Q 1/18*     (2006.01)
    *C12Q 1/68*     (2018.01)
    *C12Q 1/689*    (2018.01)

(52) U.S. Cl.
    CPC .............. *C12Q 1/18* (2013.01); *C12Q 1/689* (2013.01); *C12Q 2600/106* (2013.01); *C12Q 2600/158* (2013.01)

(58) Field of Classification Search
    CPC .... C12Q 1/18; C12Q 1/689; C12Q 2600/106; C12Q 2600/158
    See application file for complete search history.

(56) References Cited

U.S. PATENT DOCUMENTS

| | | | | |
|---|---|---|---|---|
| 6,153,400 A | * | 11/2000 | Matsumura | C12Q 1/18 435/283.1 |
| 10,233,483 B2 | * | 3/2019 | Talebpour | C12Q 1/689 |
| 2003/0138874 A1 | * | 7/2003 | Taintor | C12Q 1/04 435/34 |
| 2007/0117172 A1 | * | 5/2007 | Price | G01N 33/525 435/18 |
| 2012/0077206 A1 | * | 3/2012 | Metzger | G16B 99/00 435/7.1 |

OTHER PUBLICATIONS

Aellen et al. Detection of live and antibiotic-killed bacteria by quantitative real-time PCR of specific fragments of rRNA. Antimicrobial Agents Chemotherapy (2006) vol. 50, No. 6, pp. 1913-1920. (Year: 2006).*

* cited by examiner

*Primary Examiner* — David C Thomas
(74) *Attorney, Agent, or Firm* — Hill & Schumacher

(57) ABSTRACT

Methods are provided for performing antibiotic susceptibility testing based on the detection of RNA, such as tmRNA, from microbial cells after exposure to antibiotics. In some embodiments, aliquots are obtained from a sample, one of which contains a selected antibiotic. The aliquots, which include growth media, are incubated under conditions suitable for microbial growth, and the microbial cells in each aliquot are removed and lysed, and the lysate is subjected to reverse transcription and amplification in infer the effect of the selected antibiotic on the microbial cells. In one embodiment, a sample containing microbial cells is incubated in the presence of a selected antibiotic and a stimulus is provided to induce the production of m RNA within the microbial cells. The microbial cells are subsequently lysed without substantial degradation of the m RNA within the lysate, and the m RNA is detected to determine the effect of the antibiotic on the microbial cells.

20 Claims, 16 Drawing Sheets

Specification includes a Sequence Listing.

| Gram + | Gram - | Fung. | Staph. | Staph. aureus | Entero-coccus | Strep pneu. | Pseudo. aerug. | C. kru. /gla. | Organ-ism | Example Antibiotic(s) |
|---|---|---|---|---|---|---|---|---|---|---|
| ■ |  |  | ■ | ■ |  |  |  |  | Staph. aureus | Vanco + oxacillin |
| ■ |  |  | ■ |  |  |  |  |  | Other Staph. | Suspect contaminant |
| ■ |  |  |  |  |  | ■ |  |  | Strep. pneu. | Vanco + ceftriaxone |
| ■ |  |  |  |  | ■ |  |  |  | Enterro-coccus | Vanco + ampicillin |
| ■ |  |  |  |  |  |  |  |  | Other Strep. | Ampicillin |
|  | ■ |  |  |  |  |  |  |  | Enteroba-cteriacae | Etrapenem |
|  | ■ |  |  |  |  |  | ■ |  | P. aeru. | Ceftizoxime |
|  |  | ■ |  |  |  |  |  |  | Other fungi | Fluconazole |
|  |  | ■ |  |  |  |  |  | ■ | C. krusei C. glabrata | Mycafungin |

FIG. 5

| | rRNA | | | tmRNA | |
|---|---|---|---|---|---|
| | #1 | #2 | #3 | C | G |
| 0 hr | 22.4 | 19.7 | 26.4 | 26.0 | 31.1 |
| 2 hr | 20.7 | 17.7 | 25.8 | 20.9 | 25.8 |

| | rRNA primers | | | tmRNA primers | | | | | | |
|---|---|---|---|---|---|---|---|---|---|---|
| | #1 | #2 | #3 | A | B | C | D | E | F | G |
| Non-Treated | 19.0 | 17.3 | 24.1 | 23.5 | 24.0 | 21.7 | 22.2 | 23.7 | 23.9 | 21.7 |
| Treated with 8 ug/mL Norfloxacin | 27.9 | 25.7 | 32.6 | 31.9 | 31.9 | 30.7 | 29.9 | 32.0 | 32.0 | 28.9 |
| Treated with 8 ug/mL Tetracycline | 24.4 | 22.3 | 29.8 | 29.0 | 30.2 | 27.6 | 27.6 | 30.3 | 29.8 | 27.3 |
| Treated with 2 ug/mL Oxacillin | 19.3 | 17.8 | 30.1 | 23.1 | 24.8 | 21.8 | 22.4 | 23.9 | 24.3 | 23.1 |

SEQUENCE LISTING

<160> NUMBER OF SEQ ID NOS: 30

<210> SEQ ID NO 1
<211> LENGTH: 20
<212> TYPE: DNA
<213> ORGANISM: Artificial
<220> FEATURE:
<223> OTHER INFORMATION: Pan enterobacter primer

<400> SEQUENCE: 1
acaagcggtg gagcatgtgg                                          20

<210> SEQ ID NO 2
<211> LENGTH: 24
<212> TYPE: DNA
<213> ORGANISM: Artificial

```
<220> FEATURE:
<223> OTHER INFORMATION: Pan enterobacter primer

<400> SEQUENCE: 2
gcgggactta acccaacatt tcac                                          24

<210> SEQ ID NO 3
<211> LENGTH: 26
<212> TYPE: DNA
<213> ORGANISM: Artificial
<220> FEATURE:
<223> OTHER INFORMATION: E. coli and K. pneumoniae primer

<400> SEQUENCE: 3
gcaaacgacg aaaactacgc tttagc                                        26

<210> SEQ ID NO 4
<211> LENGTH: 23
<212> TYPE: DNA
<213> ORGANISM: Artificial
<220> FEATURE:
<223> OTHER INFORMATION: E. coli and K. pneumoniae primer

<400> SEQUENCE: 4
cctacatcct cggtactaca tgc                                           23

<210> SEQ ID NO 5
<211> LENGTH: 21
<212> TYPE: DNA
<213> ORGANISM: Artificial
<220> FEATURE:
<223> OTHER INFORMATION: Pan enterobacter primer

<400> SEQUENCE: 5
gtgcccttga ggcgtggctt c                                             21

<210> SEQ ID NO 6
<211> LENGTH: 23
<212> TYPE: DNA
<213> ORGANISM: Artificial
<220> FEATURE:
<223> OTHER INFORMATION: Pan enterobacter primer

<400> SEQUENCE: 6
gcgggactta accgaacatt cac                                           23

<210> SEQ ID NO 7
<211> LENGTH: 20
<212> TYPE: DNA
<213> ORGANISM: Artificial
<220> FEATURE:
<223> OTHER INFORMATION: Pan enterobacter primer

<400> SEQUENCE: 7
acaagcggtg gagcatgtgg                                               20

<210> SEQ ID NO 8
<211> LENGTH: 24
<212> TYPE: DNA
<213> ORGANISM: Artificial
<220> FEATURE:
<223> OTHER INFORMATION: Pan enterobacter primer

<400> SEQUENCE: 8
gcgggactta acccaacatt tcac                                          24
```

```
<210> SEQ ID NO 9
<211> LENGTH: 20
<212> TYPE: DNA
<213> ORGANISM: Artificial
<220> FEATURE:
<223> OTHER INFORMATION: Pan enterobacter primer

<400> SEQUENCE: 9
actttcagcg gggaggaagg                                                    20

<210> SEQ ID NO 10
<211> LENGTH: 24
<212> TYPE: DNA
<213> ORGANISM: Artificial
<220> FEATURE:
<223> OTHER INFORMATION: Pan enterobacter primer

<400> SEQUENCE: 10
gcgggactta acccaacatt tcac                                               24

<210> SEQ ID NO 11
<211> LENGTH: 26
<212> TYPE: DNA
<213> ORGANISM: Artificial
<220> FEATURE:
<223> OTHER INFORMATION: E. coli and K. pneumoniae primer

<400> SEQUENCE: 11
gcaaacgacg aaaactacgc tttagc                                             26

<210> SEQ ID NO 12
<211> LENGTH: 23
<212> TYPE: DNA
<213> ORGANISM: Artificial
<220> FEATURE:
<223> OTHER INFORMATION: E. coli and K. pneumoniae primer

<400> SEQUENCE: 12
gcttagtcag tctttacatt cgc                                                23

<210> SEQ ID NO 13
<211> LENGTH: 26
<212> TYPE: DNA
<213> ORGANISM: Artificial
<220> FEATURE:
<223> OTHER INFORMATION: E. coli and K. pneumoniae primer

<400> SEQUENCE: 13
gcaaacgacg aaaactacgc tttagc                                             26

<210> SEQ ID NO 14
<211> LENGTH: 20
<212> TYPE: DNA
<213> ORGANISM: Artificial
<220> FEATURE:
<223> OTHER INFORMATION: E. coli and K. pneumoniae primer

<400> SEQUENCE: 14
cggacggaca cgccactaac                                                    20

<210> SEQ ID NO 15
<211> LENGTH: 26
<212> TYPE: DNA
<213> ORGANISM: Artificial
<220> FEATURE:
<223> OTHER INFORMATION: E. coli and K. pneumoniae primer
```

```
<400> SEQUENCE: 15
gcaaacgacg aaaactacgc tttagc                                          26

<210> SEQ ID NO 16
<211> LENGTH: 23
<212> TYPE: DNA
<213> ORGANISM: Artificial
<220> FEATURE:
<223> OTHER INFORMATION: E. coli and K. pneumoniae primer

<400> SEQUENCE: 16
cctacatcct cggtactaca tgc                                             23

<210> SEQ ID NO 17
<211> LENGTH: 23
<212> TYPE: DNA
<213> ORGANISM: Artificial
<220> FEATURE:
<223> OTHER INFORMATION: E. coli and K. pneumoniae primer

<400> SEQUENCE: 17
gggatttgcg aaacccaagg tgc                                             23

<210> SEQ ID NO 18
<211> LENGTH: 23
<212> TYPE: DNA
<213> ORGANISM: Artificial
<220> FEATURE:
<223> OTHER INFORMATION: E. coli and K. pneumoniae primer

<400> SEQUENCE: 18
gttttaacgc ttcaacccca ggc                                             23

<210> SEQ ID NO 19
<211> LENGTH: 23
<212> TYPE: DNA
<213> ORGANISM: Artificial
<220> FEATURE:
<223> OTHER INFORMATION: E. coli and K. pneumoniae primer

<400> SEQUENCE: 19
gggatttgcg aaacccaagg tgc                                             23

<210> SEQ ID NO 20
<211> LENGTH: 23
<212> TYPE: DNA
<213> ORGANISM: Artificial
<220> FEATURE:
<223> OTHER INFORMATION: E. coli and K. pneumoniae primer

<400> SEQUENCE: 20
gcttagtcag tctttacatt cgc                                             23

<210> SEQ ID NO 21
<211> LENGTH: 23
<212> TYPE: DNA
<213> ORGANISM: Artificial
<220> FEATURE:
<223> OTHER INFORMATION: E. coli and K. pneumoniae primer

<400> SEQUENCE: 21
gggatttgcg aaacccaagg tgc                                             23

<210> SEQ ID NO 22
```

```
<211> LENGTH: 20
<212> TYPE: DNA
<213> ORGANISM: Artificial
<220> FEATURE:
<223> OTHER INFORMATION: E. coli and K. pneumoniae primer

<400> SEQUENCE: 22
cggacggaca cgccactaac                                                   20

<210> SEQ ID NO 23
<211> LENGTH: 23
<212> TYPE: DNA
<213> ORGANISM: Artificial
<220> FEATURE:
<223> OTHER INFORMATION: E. coli and K. pneumoniae primer

<400> SEQUENCE: 23
gggatttgcg aaacccaagg tgc                                               23

<210> SEQ ID NO 24
<211> LENGTH: 23
<212> TYPE: DNA
<213> ORGANISM: Artificial
<220> FEATURE:
<223> OTHER INFORMATION: E. coli and K. pneumoniae primer

<400> SEQUENCE: 24
cctacatcct cggtactaca tgc                                               23

<210> SEQ ID NO 25
<211> LENGTH: 23
<212> TYPE: DNA
<213> ORGANISM: Artificial
<220> FEATURE:
<223> OTHER INFORMATION: E. coli primer

<400> SEQUENCE: 25
gtactaccaa ctcttgtgta gcg                                               23

<210> SEQ ID NO 26
<211> LENGTH: 22
<212> TYPE: DNA
<213> ORGANISM: Artificial
<220> FEATURE:
<223> OTHER INFORMATION: E. coli primer

<400> SEQUENCE: 26
agcagcaata attttgaacg gc                                                22

<210> SEQ ID NO 27
<211> LENGTH: 24
<212> TYPE: DNA
<213> ORGANISM: Artificial
<220> FEATURE:
<223> OTHER INFORMATION: E. coli primer

<400> SEQUENCE: 27
agtacgcacg gtatcagcag caat                                              24

<210> SEQ ID NO 28
<211> LENGTH: 22
<212> TYPE: DNA
<213> ORGANISM: Artificial
<220> FEATURE:
<223> OTHER INFORMATION: E. coli primer

<400> SEQUENCE: 28
```

```
gcagcacggt tttgaacggc at                                              22

<210> SEQ ID NO 29
<211> LENGTH: 23
<212> TYPE: DNA
<213> ORGANISM: Artificial
<220> FEATURE:
<223> OTHER INFORMATION: E. coli primer

<400> SEQUENCE: 29
gtactaccaa ctcttgtgta gcg                                             23

<210> SEQ ID NO 30
<211> LENGTH: 24
<212> TYPE: DNA
<213> ORGANISM: Artificial
<220> FEATURE:
<223> OTHER INFORMATION: E. coli primer

<400> SEQUENCE: 30
agtacgcacg gtatcagcag caat                                            24
```

METHODS OF TARGETED ANTIBIOTIC SUSCEPTIBILITY TESTING

CROSS-REFERENCE TO RELATED APPLICATION

This application claims priority to U.S. Provisional Application No. 61/842,827, titled "METHODS OF TARGETED ANTIBIOTIC SUSCEPTIBILITY TESTING" and filed on Jul. 3, 2013, the entire contents of which is incorporated herein by reference.

BACKGROUND

This disclosure relates to methods of determining the antibiotic susceptibility of microbial cells in a sample. This disclosure also relates to methods of measuring RNA in microbial cells.

Emergence of drug resistant pathogens is a global healthcare crisis that is forcing physicians to treat common infectious diseases with ever more expensive, potent, and sometimes more toxic antibiotics. Unfortunately, pharmaceutical development of new antibiotics has rapidly declined, resulting in a lack of new agents to treat some organisms that are multi-drug resistant. Mainstream clinical microbiology is slow and expensive because it still relies on bacterial growth for colony formation on agar plates, a time-consuming, labour-intensive method requiring skilled technicians who are increasingly in short supply. Antibiotic susceptibility data are typically not available for 2-3 days after specimen acquisition, which is too late to meaningfully impact antibiotic selection. New rapid clinical microbiology methods are urgently needed that can perform identification and antibiotic susceptibility testing (AST) directly on pathogens found in clinical specimens, providing clinicians with real-time information to manage infectious diseases.

In the absence of an expeditious microbiologic diagnosis, clinicians typically initiate "empiric" antibiotic treatment, meaning that antibiotics are chosen based on knowledge of potential organisms and their antibiotic resistance patterns. Empiric antibiotics for bacteremia are typically broad-spectrum antibiotics to treat a wide variety of possible bacterial pathogens. Overuse of broad-spectrum antibiotics contributes to the emergence of antibiotic resistance by applying selective pressure to the patient's microbiota and favoring colonization by resistant organisms. For example, the common use of vancomycin and piperacillin-tazobactam as empiric therapy has contributed directly to the widespread emergence of vancomycin-resistant enterococci (VRE) and extended-spectrum beta-lactamase (ESBL) producing *E. coli* and *Klebsiella pneumoniae* organisms. In contrast, fungemia is frequently not suspected or treated until patients receiving antibacterial agents do not respond or experience clinical deterioration. Evidence suggests that the use of early, effective antibiotic therapy improves patient outcomes and shortens hospital length of stay. Therefore, the ability to quickly identify the causative organism(s) and administer appropriate antibiotic therapy should result in improved patient outcomes as well as reduce overall costs to the healthcare system.

SUMMARY

Methods are provided for performing antibiotic susceptibility testing based on the detection of RNA, such as ribosomal or transfer messenger RNA, from microbial cells after exposure to antibiotics. In some embodiments, aliquots are obtained from a sample, one of which contains a selected antibiotic. The aliquots, which include growth media, are incubated under conditions suitable for microbial growth, and the microbial cells in each aliquot are removed and lysed, and the lysate is subjected to reverse transcription and amplification infer the effect of the selected antibiotic on the microbial cells. In one embodiment, a sample containing microbial cells is incubated in the presence of a selected antibiotic and a stimulus is provided to induce the production of mRNA within the microbial cells. The microbial cells are subsequently lysed without substantial degradation of the mRNA within the lysate, and the mRNA is detected to determine the effect of the antibiotic on the microbial cells.

Accordingly, in a first aspect, there is provided a method of performing rapid antibiotic susceptibility testing, comprising:

performing a multiplexed identification test panel on a first lysate, the first lysate having been obtained from a first sample that is suspected of containing microbial cells;

obtaining, from a second sample that is suspected of containing the microbial cells, at least a primary aliquot and a reference aliquot, wherein the primary aliquot and the reference aliquot comprise growth media, and wherein the first sample and the second sample are derived from a common subject;

adding, to the primary aliquot, at least one selected antibiotic, the selected antibiotic having been selected, at least in part, based on the results of the multiplexed identification test panel;

incubating the primary aliquot and the reference aliquot under conditions suitable for promoting microbial growth for testing the effectiveness of the selected antibiotic;

separating microbial cells from the primary aliquot and resuspending the separated microbial cells to obtain a primary suspension;

separating microbial cells from the reference aliquot and resuspending the separated microbial cells to obtain a reference suspension;

lysing the microbial cells in the primary suspension and the reference suspension, thereby obtaining a primary lysate and a reference lysate;

performing reverse transcription and amplification on the primary lysate and to detect nucleic acids associated with microbial cells detectable by the multiplexed identification test panel, thereby obtaining a primary assay signal;

performing reverse transcription and amplification on the reference lysate to detect nucleic acids associated with microbial cells detectable by the multiplexed identification test panel identification panel, thereby obtaining a reference assay signal;

comparing the primary assay signal and the reference assay signal to obtain a measure of the effectiveness of the selected antibiotic against the microbial cells.

In another aspect, there is provided a method of performing rapid antibiotic susceptibility testing, comprising:

obtaining, from a sample that is suspected of containing microbial cells, at least a primary aliquot and a reference aliquot, wherein the primary aliquot and the reference aliquot comprise growth media;

adding, to the primary aliquot, at least one selected antibiotic;

incubating the primary aliquot and the reference aliquot under conditions suitable for promoting microbial growth for testing the effectiveness of the selected antibiotic;

separating microbial cells from the primary aliquot and resuspending the separated microbial cells to obtain a primary concentrated suspension;

separating microbial cells from the reference aliquot and resuspending the separated microbial cells to obtain a reference concentrated suspension;

lysing the microbial cells in the primary concentrated suspension and the reference concentrated suspension, thereby obtaining a primary lysate and a reference lysate;

performing reverse transcription and amplification on the primary lysate and the reference lysate to detect nucleic acids associated with members of a microbial test panel, thereby obtaining a primary assay signal and a reference assay signal;

comparing the primary assay signal and the reference assay signal to obtain a measure of the effectiveness of the selected antibiotic against the microbial cells.

In another aspect, there is provided a method of performing rapid antibiotic susceptibility testing, comprising:

obtaining, from a sample that is suspected of containing microbial cells, a plurality of primary aliquots and a reference aliquot, wherein the primary aliquots and the reference aliquot comprise growth media;

adding, to each primary aliquot, at least one selected antibiotic, such that at least two of the primary aliquots comprise different selected antibiotics;

incubating the primary aliquots and the reference aliquot under conditions suitable for promoting microbial growth for testing the effectiveness of the selected antibiotics;

separating microbial cells from the primary aliquots and resuspending the separated microbial cells to obtain a plurality of primary suspensions;

separating microbial cells from the reference aliquot and resuspending the separated microbial cells to obtain a reference suspension;

lysing the microbial cells in the primary suspensions and the reference suspension, thereby obtaining a plurality of primary lysates and a reference lysate;

performing reverse transcription and amplification on the primary lysates and the reference lysate to detect nucleic acids associated with members of a microbial panel, thereby obtaining a plurality of primary assay signals and a reference assay signal;

comparing the primary assay signals and the reference assay signal to obtain a measure of the effectiveness of the selected antibiotics against the microbial cells.

In another aspect, there is provided a method of performing rapid antibiotic susceptibility testing, comprising:

obtaining, from a sample that is suspected of containing microbial cells, at least a primary aliquot and a reference aliquot, wherein the primary aliquot and the reference aliquot comprise growth media;

adding, to the primary aliquot, at least one selected antibiotic;

incubating the primary aliquot and the reference aliquot under conditions suitable for promoting microbial growth for testing the effectiveness of the selected antibiotic;

subjecting the microbial cells in the primary aliquot and the reference aliquot to a stimulus configured to induce the production of a target mRNA, wherein the stimulus is selected such that the production of mRNA for susceptible and/or resistant microbial cells is altered due to exposure of the microbial cells to the selected antibiotic;

lysing the microbial cells in the primary aliquot and the reference aliquot to obtain a primary lysate and a secondary lysate, wherein the lysis is performed in a manner suitable for avoiding substantial degradation of the mRNA in each lysate, and wherein the lysis is performed on a timescale associated with the lifetime of mRNA produced in the microbial cells in response to the stimulus;

performing reverse transcription and amplification on the primary lysate and the reference lysate to detect mRNA associated with members of a microbial test panel, thereby obtaining a primary assay signal and a reference assay signal;

comparing the primary assay signal and the reference assay signal to obtain a measure of the effectiveness of the selected antibiotic against the microbial cells.

In another aspect, there is provided a method of performing antibiotic susceptibility testing, comprising:

obtaining at least a primary aliquot and a reference aliquot from a sample suspected of containing microbial cells;

adding at least one selected antibiotic to the primary aliquot;

lysing microbial cells obtained from the primary aliquot and the reference aliquot, thereby obtaining a primary lysate and a reference lysate;

performing reverse transcription and amplification on the primary lysate and to detect tmRNA associated with members of a test panel, thereby obtaining a primary assay signal;

performing reverse transcription and amplification on the reference lysate to detect nucleic acids associated with the members of test panel, thereby obtaining a reference assay signal;

comparing the primary assay signal and the reference assay signal to obtain a measure of the effectiveness of the selected antibiotic against the microbial cells.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 5 is an identification test panel in which members of the identification panel have one or more corresponding antibiotics associated therewith. In some embodiments, such identification-antibiotic correspondence information (optionally further classified according to sample type, type of infection (nosocomial or community acquired), and hospital ward origin) can be employed to select one or more antibiotics for antibiotic susceptibility testing, as a reflex test, without requiring input from a medical practitioner.

DETAILED DESCRIPTION

Figure 1A:
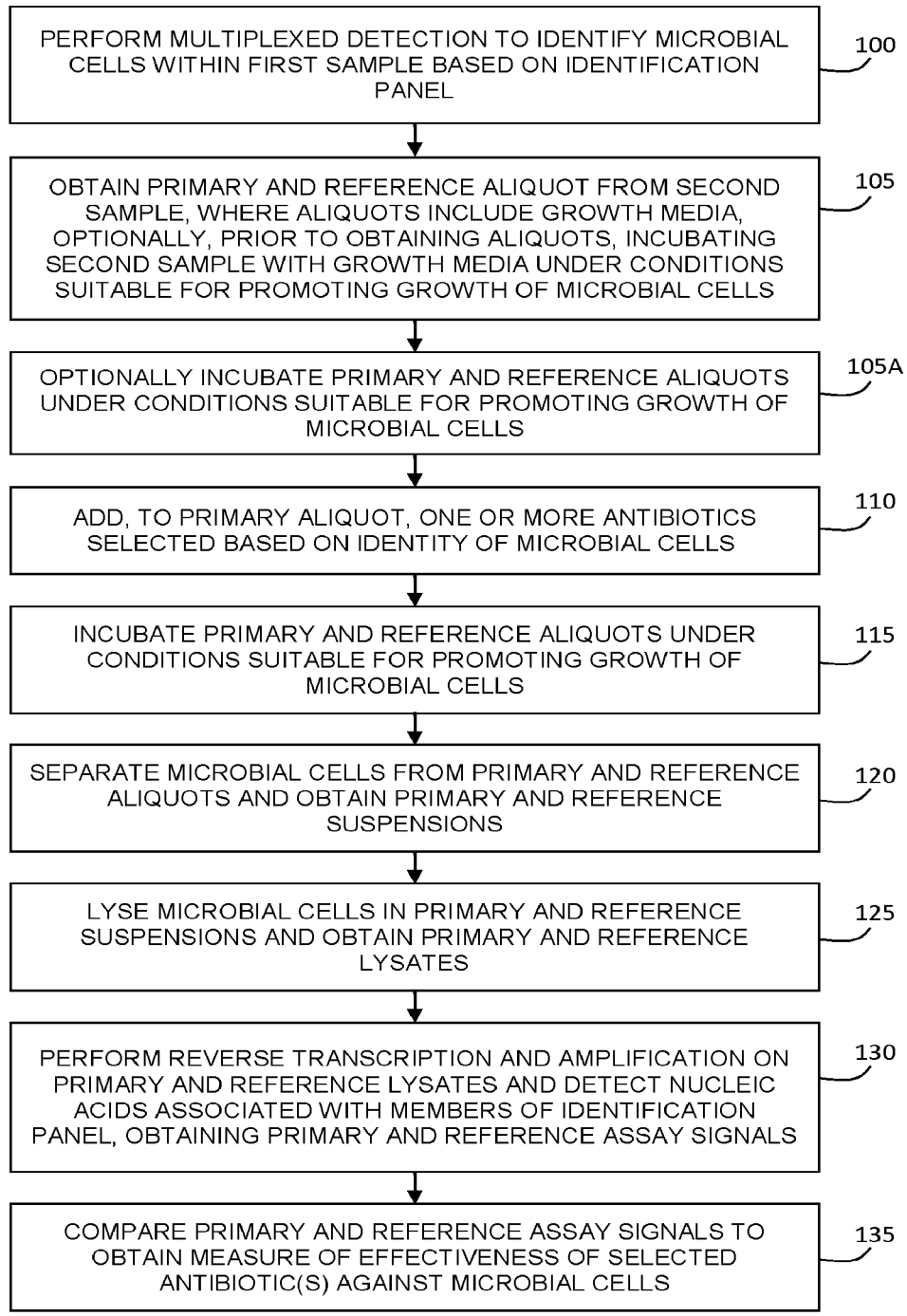
FIG. 1A is a flow chart illustrating an example implementation of a method for determining the antibiotic susceptibility of microbial cells in a sample, where the identity of microbial cells is initially determined based on an identification panel, after which a sample aliquot is exposed to one or more antibiotics, where the one or more antibiotics are selected based on the previously determined identity of the microbial cells. The antibiotic effectiveness is determined by performing a reverse transcription and amplification assay after separating the microbial cells from the aliquot and lysing the separated microbial cells, and comparing the assay signal to a reference assay signal obtained from a reference aliquot.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

The term "antibiotic susceptibility testing", as used herein, refers to the testing of the effect of an antibiotic on microbial cells, in order to provide a measure that may be employed in order to estimate or determine the likelihood of success of in-vivo therapeutic treatment involving the antibiotic.

The present disclosure provides various example methods for performing rapid antibiotic susceptibility testing of an antibiotic selected based on the identification of the microbial cells. Some example embodiments of the present disclosure support the estimation or determination of susceptibility or resistance directly from patient samples in a short time period, prior to the availability of culture results, thereby meaningfully impacting antimicrobial therapy prior to the availability of conventional identification and antibiotic susceptibility results.

According to some embodiments, antibiotic susceptibility testing may be performed after having first obtained information associated with the identify of microbial cells within a sample (e.g. the kingdom, genus, family, species, strain, Gram stain status, or another identifying characteristic, such as a molecular sequence belonging to DNA or RNA of the microbial cell), such that one or more candidate antibiotics may be selected.

FIG. 1A illustrates one example method of performing such a rapid assessment of the effectiveness of an antibiotic that is selected based results from an initial multiplexed identification test panel. As shown at 100 in FIG. 1A, an initial multiplexed detection step is performed, in order to identify the microbial cells within a first sample, such that the microbial cells are identified based on results from a multiplexed identification test panel.

The test panel may include multiple levels of identification, including, for example, multiplexed tests for kingdom (e.g. fungal vs. bacterial), genus, species, Gram stain status (e.g. the panel may include separate tests for Gram-negative microbial species and Gram positive microbial species, based on nucleic acid sequences that pertain to a subset of clinically relevant bacterial species), and optionally strain. An example of such a test panel is shown in FIG. 5. Accordingly, in some embodiments, when the test is conducted on a sample containing a given type of microbial cell, multiple forms of information may be provided by the multiplexed identification test panel, such as Gram stain status, genus, and species. For example, as shown in FIG. 5, when a given microbial cell type is analyzed, a plurality of tests of the multiplexed identification test panel may be positive, such a test related to kingdom (e.g. bacteria), a test based on Gram stain status (e.g. Gram positive), a test based on genus (e.g. *Staphylococcus*), and a test based on species (e.g. *Staphylococcus aureus*). Accordingly, the multiplexed identification test panel need not necessarily provide direct identification, but may instead provide one or more test results that narrow the range of possible microbial cell types, in a manner analogous to results from a Gram stain and morphology test result.

In some embodiments, the initial test may be a test that is performed post-culture, involving a test modality that requires a higher quantity of microbial cells. For example, if the sample is a positive blood culture sample, methods such as conventional phenotypic testing, fluorescence in-situ hybridization, and MALDI-based detection may be employed (in some cases, it may be necessary to first obtain an isolate via subculture).

In the present example embodiment, the initial multiplexed identification test and initial antibiotic susceptibility test are performed such that both the identification results and antibiotic susceptibility results are available prior to conventional culture results. For example, in some example embodiments, the present methods may be performed based on a direct, uncultured sample. In other example embodiments, the present methods may be performed based on a sample that has been initially exposed to growth media and incubated, but has not yet produced a positive culture result by conventional culture such as blood culture or plate-based colony growth).

In embodiments in which the sample is an uncultured sample with a low count of microbial cells, the initial multiplexed identification test may be performed according to a wide variety of rapid multiplexed methods, where the selected method may depend on the nature of the sample. Examples of direct sample identification methods include a molecular method such as the LightCycler® SeptiFast Test MGRADE, Sepsitest™, and YVOO® protocols. It is understood that non-amplification methods may also optionally be employed, provided that the sample preparation method that is employed has a sufficiently high recovery and/or if the microbial cell count in the sample is sufficiently high (for example, non-amplification methods may be employed for urine samples, which typically have microbial cell counts of $\sim >10^4$ CFU/ml).

In another example implementation, the identification of the microbial cells within an uncultured sample may be performed according to sample preparation, lysis, and/or detection methods disclosed in US Patent Publication No. 2014/0154687, titled "APPARATUS AND METHOD FOR PRETREATMENT OF MICROBIAL SAMPLES" and filed on Mar. 15, 2013, which is hereby incorporated by reference in its entirety.

Briefly, according to an example implementation of US Patent Publication No. 2014/0154687, pretreatment of an uncultured sample may be performed via the optional initial selective lysis, within a sample pretreatment vessel, of non-microbial cells (such as blood cells) and the subsequent centrifugation of the sample to remove the resulting debris and concentrate the microbial cells. An immiscible and dense cushioning liquid may be included for collecting the microbial cells adjacent to the liquid interface formed by the cushioning liquid, upon centrifugation of the pretreatment vessel. After removal of a substantial quantity of the supernatant, resuspension of the collected microbial cells, and re-establishment of the liquid interface, at least a portion of the remaining suspension is removed without substantially removing the cushioning liquid and the collected microbial cells. One or more intermediate wash cycles may be performed prior to extraction of the processed sample, which provides a "pretreated" sample.

The extracted suspension of microbial cells is then subjected to a lysis process, prior to identification via multiplexed nucleic acid amplification. One example lysis method may involve removal of the potential PCR inhibitors and nucleases in the cell suspension followed by performing a rapid lysis protocol, such as bead beating with or without ultrasonic irradiation, in a lysis buffer that may include nuclease inhibitors. These methods involve multiple steps and reagents, and often require subsequent purification steps prior to performing PCR.

In one example implementation, an electrical lysis method may be employed, such as the electrical lysis method disclosed in US Patent Publication No. 2014/0004501, titled "METHODS AND DEVICES FOR ELECTRICAL SAMPLE PREPARATION" and filed on Jan. 25, 2013. This method involves subjecting the cell suspension to a train of pulsed electrical fields in a microfluidic channel.

The upper and lower electrodes of the channel are separated by a thin insulator spacer, defining the channel gap. The channel, may employ valves in both inlet and outlet channels to assist in controlling evaporation of the liquid during electrical lysing and treatment, to maintain a suitable pressure within the channel during processing, and to control the exposure of the fluid to electrical field and thermal effects. The application of a bipolar electric pulse train on the two electrodes, establishes an electric field in the electric chamber results in ionic current and Joule heating of the liquid. In one embodiment, the amplitude and the number of pulses are chosen such that the microbial cells are subjected to an electric field of more than 5 kV/cm and the channel temperature reach to at least 120° C. in less than 50 ms. Such conditions have been found to be suitable for the rapid lysis of a broad range of microbial cell types. As the duration of the electric pulse train and, consequently, the accompanying Joule heating, is brief, this mechanism of heating is referred to as "flash heating". The coupled effect of the electric field acting on the cells and the flash heating of the liquid causes the microbial cells to lyse and intracellular molecules, such as proteins and nucleic acids, to be released from the cell ("E-lysis") as a lysate. In addition, some of the macromolecular content of the cell may undergo a transformation in the period between the application of the electric field and cooling down of the liquid. This process, identified herein as electrical-treatment ("E-treatment"), has been found to render nucleic acids, such as rRNA and gDNA, more accessible to enzymes, thus improving the efficiencies of the ensuing nucleic acid amplification processes. Moreover, the E-treatment method has been found to denature and/or inactivates proteins and enzymes such as nucleases and other PCR inhibitory contaminants. Thus the combined E-lysis and E-treatment processes may be employed to yield a lysate that is ready and suitable for nucleic acid based assays.

After having obtained a lysate of the first sample, a multiplexed nucleic acid detection step is performed to identify the microbial cells in the sample. In one example, the detection step may employ gDNA, such as, for example, the amplification methods employed by the LightCycler® SeptiFast Test MGRADE, Sepsitest™, and YVOO® protocols described above. In another example embodiment, the multiplexed detection may be achieved via the reverse transcription and multiplexed amplification of rRNA, as disclosed in US Patent Publication No. 2014/0154687 and US Patent Publication No. 2014/0004501.

Referring again to FIG. 1A, after having identified the microbial cells according to the identification panel, one or more suitable antibiotics may be selected and employed for antibiotic susceptibility testing according to steps 105-135.

In one example implementation, the one or more selected antibiotics may be selected by a medical practitioner, based on the identified microbial cells. In such a case, the medical practitioner may select the one or more selected antibiotics based on (at least) the results of the multiplexed identification test panel and the antibiogram. In such an embodiment, the selected antibiotic is thus the antibiotic that is prescribed to the patient based on the decision made by the medical practitioner. Such an embodiment may involve a considerable time delay, due to the time delay involved in the communication of the identification results to the medical practitioner, and the time delay involved in receiving the choice of the selected antibiotic.

In another example embodiment, the selected antibiotic may be selected, without requiring consultation or input from a medical practitioner (i.e. without providing the identification results to the medical practitioner and awaiting the medical practitioner's antibiotic selection), and the subsequent antibiotic susceptibility testing may be performed as a reflex test. In such an embodiment, the selection of the antibiotic may be based on identification-antibiotic correspondence information that associates various combinations of results from the multiplexed identification tests with one or more antibiotics. An example of such an association is shown in FIG. 5, where different combinations of results from the multiplexed identification test panel are associated with one or more selected antibiotics.

Accordingly, it will be understood that the present reflex-based embodiment need not involve the selection of an antibiotic for prescription/therapeutic purposes, but rather involves that determination of an antibiotic that is likely to be selected by a medical practitioner. As a result, the assessment of the effectiveness of the selected antibiotic (e.g. according to steps 105-130, or according to other methods disclosed herein or variations thereof) may be commenced without having to await the feedback from a medical practitioner, which enables the rapid assessment of antibiotic effectiveness, and the rapid communication of actionable information to a medical practitioner.

In some embodiments, the identification-antibiotic correspondence information is further classified according to one or more of sample type, type of infection (nosocomial or community acquired), and hospital ward origin, or other categories that may affect the choice of antibiotics. For example, the information shown in FIG. 5, which provides associated antibiotics for each relevant combination of test results, may be provided as a series of tables, or as a composite table, decision tree, spreadsheet, or, for example, as a dataset (including database information that can be electronically queried), where associated antibiotics are further segmented according to sample type, type of infection (nosocomial or community acquired), and/or hospital ward origin. This further segmentation of the antibiotics that are associated with a given combination of test results from the multiplexed identification test panel may be beneficial in providing antibiotic selection that has a higher likelihood of matching the antibiotic that is prescribed by a medical practitioner. This information may be updated, for example, on a periodic basis, in order to ensure that the identification-antibiotic correspondence information is representative of the current antibiogram data and optionally current hospital outbreaks (or risks of outbreaks) of resistant organisms.

Referring again to FIG. 1A, after the one or more selected antibiotics have been selected, at least two aliquots of the sample are obtained at step 105, where the aliquots are henceforth referred to as a primary and a reference aliquot. As described below, the primary aliquot is subsequently employed for exposure to a selected antibiotic, and the reference aliquot is employed as a control. After addition of a selected antibiotic to the primary aliquot and subsequent incubation of the primary and reference aliquots, reverse transcription and amplification is performed on microbial cells separated from the primary and reference aliquots in order to determine a measure of the effectiveness of the selected antibiotic on the microbial cells. The steps in performing this method are described in detail below.

Both the primary and reference aliquots contain growth media, where the growth media may be added to the aliquots, or may be added to the sample prior to the division of the sample into the aliquots. In cases where the test panel includes both aerobic and anaerobic microbial cells, at least two primary aliquots may be provided, with at least one primary aliquot being provided for aerobic growth, and at least one other primary aliquot being provided for anaerobic growth.

As shown in step 105, the primary and reference aliquots are obtained from a second sample, where both the first sample and the second sample pertain to the same subject or patient. The second sample may be a separate sample from the first sample. For example, in the case of whole blood samples, the second sample may be obtained as an additional tube (e.g. another Vacutainer™ tube). In other embodiments, the second sample may be obtained from the first sample, for example, as an aliquot of the first sample, or vice versa.

If the growth media is added to the sample prior to the division of the sample into the aliquots, the sample may be pre-incubated under conditions suitable for promoting microbial growth (e.g. a suitable temperature and environment). Similarly, as shown at step 105, the aliquots may be pre-incubated under conditions suitable for promoting microbial growth (e.g. a suitable temperature and environment, and over a time duration exceeding at least one doubling time of the microbial cells, for example at least a half an hour, or at least an hour or two hours if an initial time delay is needed in order for the microbial cells to achieve log-phase growth).

This initial pre-incubation phase is well suited for antibiotic susceptibility testing of uncultured samples that contain low numbers of microbial cells. For example, in some implementations, the pre-incubation step described herein may be employed for antibiotic susceptibility testing of samples with a very low number of microbial cells. For example, samples such as whole blood generally contain very few microbial cells when a patient is septic, such as less than 10 microbial cells in some cases. In such cases with a very low count of microbial cells, the need to subdivide a sample into multiple aliquots can be problematic due to statistical errors that may occur during the sampling process, which may impair the accuracy and value of subsequent comparisons among the aliquots (where the comparisons are made for the determination of the effectiveness of the one or more antibiotics added to the primary aliquot, as described below). Accordingly, the pre-incubation phase may be employed to increase the number of microbial cells prior to division of the sample into aliquots, such that the numbers of microbial cells within each aliquot are less prone to statistical sampling variations.

Figure 1B:
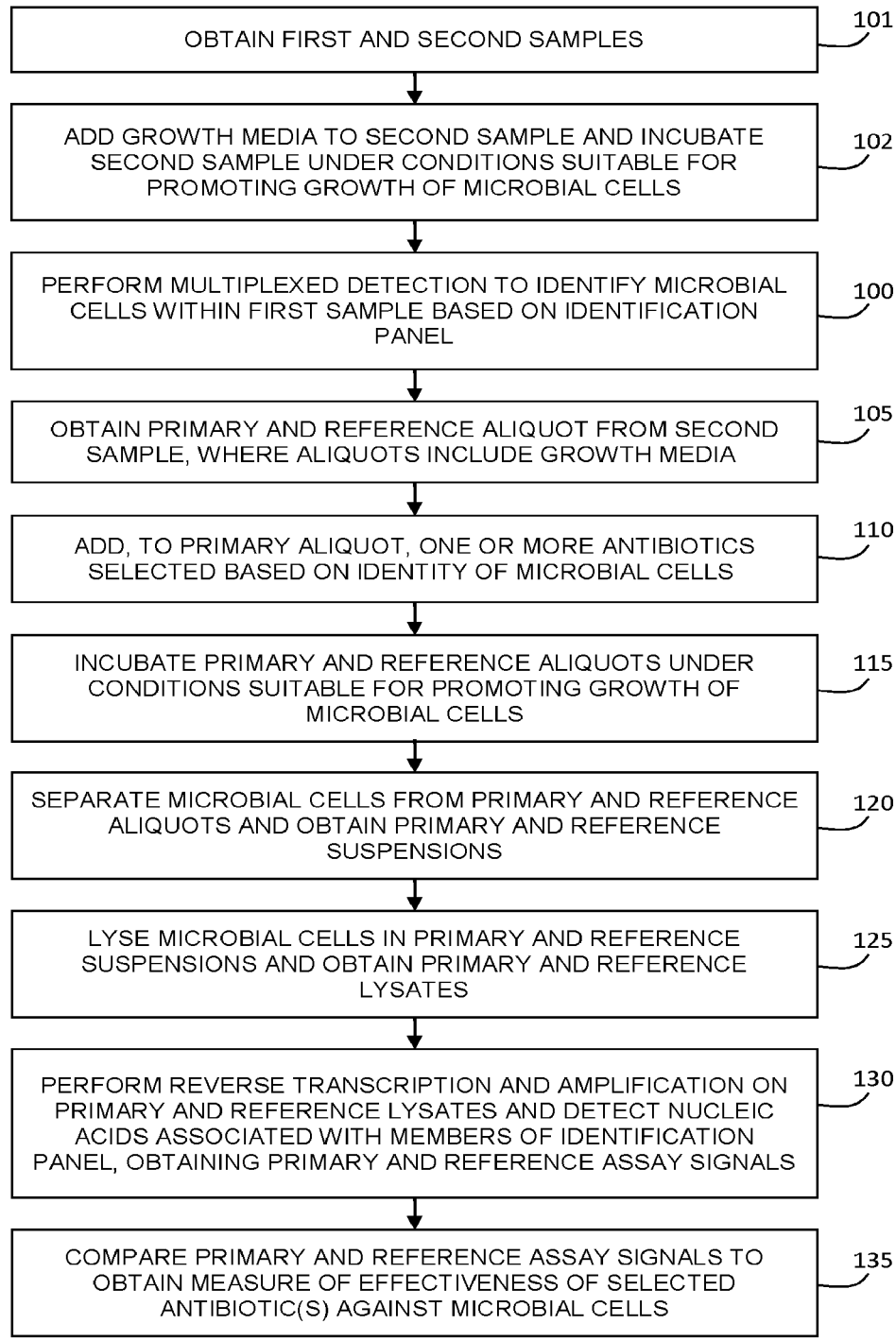
FIG. 1B is a flow chart illustrating another example implementation of a method for determining the antibiotic susceptibility of microbial cells in a sample, where the sample, upon which antibiotic sensitivity testing is performed, is initially pre-incubated with growth media during the identification test.

FIG. 1B illustrates one example alternative method of performing pre-incubation that may be beneficial in providing additional time for growth of microbial cells prior to performing the antibiotic susceptibility testing portion of the method. As shown in step 101, both the first and second sample are obtained in step 101, prior to performing the multiplexed identification test panel. As noted above, the second sample may be separately obtained relative to the first sample, or may be obtained from the first sample (e.g. as an aliquot of the first sample). In step 102, growth media is added to the second sample (alternatively, the second sample can be collected into a container or vessel that contains growth media), and the second sample is incubated under conditions suitable for the growth of microbial cells.

As shown at step 110, a quantity of the one or more selected antibiotics is added to the primary aliquot (it is noted that the vessel into which the sample is divided to obtain the primary aliquot may contain the antibiotic, such that the sample is added to the antibiotic). The amount of the selected antibiotic may be determined, for example, according to known or standardized values, such as those quoted in the Clinical and Laboratory Standards Institute (CLSI) antimicrobial susceptibility testing standards. In another example implementation, the quantity of the selected antibiotic may be determined based on antibiogram data.

Accordingly, the one or more selected antibiotics are added to the primary aliquot (or to two or more primary aliquots), and at least one other aliquot is used as a reference aliquot without the antibiotic. Although the example embodiments provided herein describe the testing of a single amount or concentration of a selected antibiotic, it is to be understood that multiple amounts or concentrations of the selected antibiotic may be tested (e.g. in series or in parallel). For example, the sample may be prepared in multiple aliquots such that at least one aliquot is provided for each antibiotic amount or concentration. Embodiments with multiple antibiotic concentrations may facilitate the measurement, determination or estimation of a minimum inhibitory concentration or other measure associated with the effectiveness of the antibiotic.

As shown at step 115, the aliquots are then incubated under conditions appropriate for microbial growth (i.e. such that microbial cells would grow in the absence of the antibiotic during incubation). For example, the microbial cells may be incubated, at a suitable temperature (e.g. 37° C.), in the presence of growth media (e.g. a culture medium) suitable for growth (with or without media designed to inhibit the effect of the antibiotics, as further described below). The microbial cells may be incubated, at a suitable temperature (e.g. 37° C.), in the sample as drawn, such as directly, in blood, with the inclusion of suitable anti-clotting agents.

In some embodiments, the time duration over which the primary aliquot is incubated with the selected antibiotic may be based, at least in part, on respective doubling time of the microbial cells and mode of action of the antibiotics. For example, antimicrobial agents that interfere with cell wall synthesis block the synthesis of peptidoglycans and the mechanism of cell death is by cell lysis due to defective or weakened cell walls. Therefore, cell wall synthesis inhibitors are active only against growing bacteria. The cell death mechanism is not immediate and involves many active cellular processes. The antimicrobial agents that interfere with DNA synthesis, for instance, bind to DNA gyrase-DNA complex and interfere with the repair of broken DNA strands by DNA gyrase during DNA replication, leading to immediate bacteriostasis followed by cell death.

In some embodiments, the primary aliquot is incubated with the selected antibiotic for a time duration that is sufficiently long for the antibiotic to induce, in susceptible microbial cells, a metabolic response that affects the quantity of RNA-based nucleic acids that are obtained after performing separation of the microbial cells from the aliquots, and resuspension of the microbial cells. For example, as shown in Examples 1 and 2 below, it has been shown that a very short time delay, such as a time delay between one and two hours post-exposure, is sufficient to produce a significant change the assay signals associated with the quantity of rRNA and/or transfer messenger RNA (tmRNA) that is detected after separation and lysis of the microbial cells. It is believed that even shorter exposure times may be employed for detecting the effect of the selected antibiotic on the microbial cells in the primary aliquot relative to those in the reference aliquot, such as a time delay of between 45 minutes and one hour, or between half an hour and one hour. Such short time durations of antibiotic exposure for detecting the effect of a selected antibiotic on microbial cells in a sample permit rapid antibiotic susceptibility testing and potentially significant change in the early targeted antimicrobial therapy.

After having incubated the primary and reference aliquots, the microbial cells in the primary and reference aliquots are separated and resuspended in another liquid (e.g. a lysis liquid or buffer), such that a primary suspension and a reference suspension are obtained. The separation may be achieved by any suitable method that achieves sufficient recovery of microbial cells in the resulting primary and reference suspensions. In one example implementation, filtration, with optional washing of the retained microbial cells, may be employed.

In another embodiment, centrifugation may be employed to obtain the primary and reference suspensions. For example, the centrifugal separation method disclosed in US Patent Publication No. 2014/0154687 may be employed, where one or more washing steps may be optionally employed. Such a method has been shown to be effective in performing a high degree of purification of the residual liquid into which the microbial cells are resuspended (depending on the number of wash cycles that are employed), while maintaining a high recovery of microbial cells (e.g. greater than 90% or greater than 95%).

Without intending to be limited by theory, it is suspected that the separation of the microbial cells from the primary aliquot may be effective in removing RNA that has entered the liquid phase of the primary aliquot due to the degradation of the cell wall that is caused by the effect of the antibiotics, and/or due to changes in microbial cells that affects the efficiency of their collection via separation (e.g. the collection efficiency via centrifugation may be lower for microbial cells having been exposed to an effective antibiotic).

As shown at step 125, the primary and reference suspensions are subsequently lysed, to obtain a primary and reference lysate. This step may be performed by any lysis method that preserves the RNA that is to be detected in the subsequent reverse transcription and amplification step. For example, as noted above, the electrical lysis method disclosed in US Patent Publication No. 2014/0004501 may be effective for this step.

Reverse transcription and amplification is then performed on the primary and reference lysates, such that RNA from microbial cells detectable by the multiplexed identification test panel are detected. Accordingly, the reverse transcription and amplification assays may be performed on the primary and reference lysates as a single assay for each lysate, with each assay detecting RNA from microbial cells detectable by the multiplexed identification test panel. Alternatively, the reverse transcription and amplification tests may be performed as a spatially multiplexed test panel, where each test the panel is configured to detect RNA from one or more microbial cells detectable by the multiplexed identification test panel.

As shown at step 135, the assay signals from the tests performed on the primary and reference lysates may be compared in order to obtain a determination, estimation, or assessment of the effectiveness of the one or more selected antibiotics on the microbial cells. In one example embodiment, the reverse transcription and amplification assays may be performed for the detection of rRNA. As shown in Examples 1 and 2 below, it has been shown even after relatively short exposure times (e.g. 1-2 hours), the rRNA RT-PCR signal is significantly lower for the primary assay signal than the reference assay signal when the microbial cells in the primary aliquot are susceptible to the selected antibiotic.

In another example embodiment, the reverse transcription and amplification assays may be performed for the detection of tmRNA, or mRNA. Transfer messenger RNA (tmRNA) is unique to prokaryotes and is essential for the viability of some bacteria (Trevor J. Franklin, George Alan Snow, Biochemistry and Molecular Biology of Antimicrobial Drug Action, 2005, p. 96). In some cases, control of the cell cycle is tightly regulated by the timing of both synthesis and degradation of tmRNA (Robert A. Meyers, RNA Regulation, 2014, p. 68). Therefore, tmRNA may be selected as a suitable target for determining the viability of bacterial cells. As also shown in Examples 1 and 2 below, it has been shown even after relatively short exposure times (e.g. 1-2 hours), the tmRNA RT-PCR signal is significantly lower for the primary assay signal than the reference assay signal when the microbial cells in the primary aliquot are susceptible to the selected antibiotic.

The example methods described herein are well suited for performing rapid identification and antibiotic testing of samples prior to the availability of conventional culture results (e.g. blood cultures, or cultures of other samples such as urine, sputum, and cerebral spinal fluid). For example, the results of such a rapid, pre-culture identification and antibiotic susceptibility test methodology may be employed to modify antimicrobial therapy by narrowing the spectrum of initially-prescribed broad-spectrum antibiotics (i.e. to rapidly de-escalate broad-spectrum treatment), while also testing for the effectiveness of antibiotics selected as per the modified antimicrobial therapy. Such an approach provides guided and rapid re-vectoring of antimicrobial therapy for cases where antimicrobial therapy has already been initiated. Alternatively, in cases where antimicrobial therapy has not yet been initiated prior to the availability of test results, the methods disclosed herein may be employed to provide guided initial therapy that avoids the use of broad-spectrum antibiotics. The ability to avoid the use, or overuse, of broad spectrum antibiotics, may be beneficial in reducing the co-morbidities and increased mortality risk that is associated with broad spectrum antibiotic use. For example, such a strategy may be employed to support the delivery of treatment that avoids or reduces the risks of toxicity, secondary infections due to the eradication of natural flora, and risk of development of antibiotic resistance, which are all associated with broad spectrum antibiotic use.

Figure 1C:
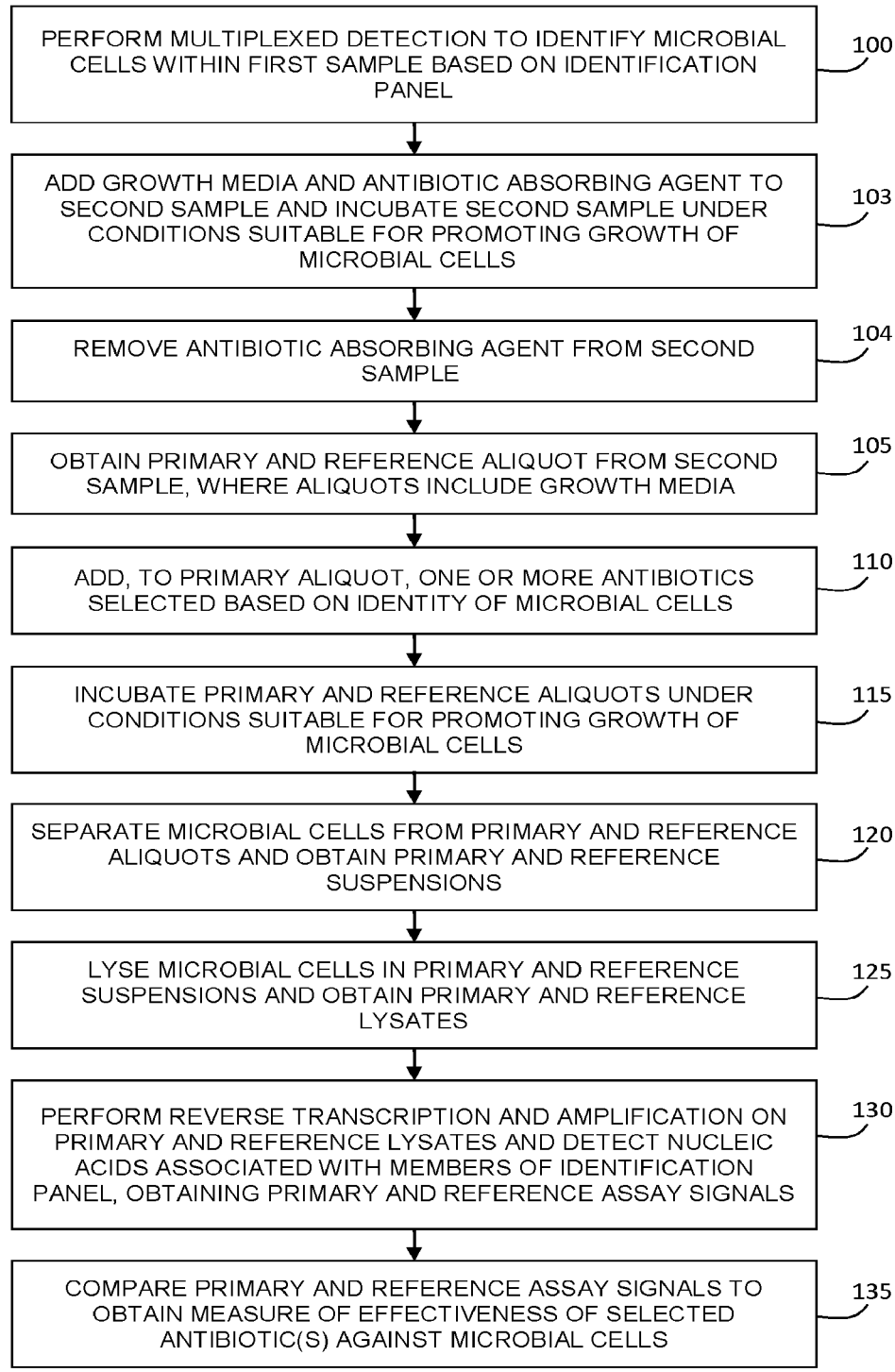
FIG. 1C is a flow chart illustrating an example implementation of a method for determining the antibiotic susceptibility of a sample, where the sample, upon which antibiotic sensitivity testing is performed, is initially pre-incubated with antibiotic absorbing agents to remove antibiotics initially present in the sample.

In some cases, the samples that are obtained may include antibiotics that were administered to the subject prior to sample collection. In such cases, it may be beneficial to extract at least a portion of the antibiotics prior to the incubation of the primary sample with the selected antibiotics. FIG. 1C illustrates an example embodiment in which antibiotic absorbing agents are added to the second sample prior to obtaining the primary aliquot.

In step 103, growth media and an antibiotic absorbing agent are added to the second sample, and the second sample is incubated under conditions suitable for promoting the growth of microbial cells. In some embodiments, this pre-incubation step may be performed for a time duration such as between a half an hour and one hour, between one hour and two hours, between two hours and three hours, between three hours and four hours, or more than four hours, depending on the effectiveness and concentration of the antibiotic absorbing agent. Furthermore, although step 103 is shown in FIG. 1C as occurring after the performing the multiplexed identification test panel, it may be alternatively be performed prior to step 100. Examples of antibiotic absorbing agents are charcoal particles and antibiotic binding resins (e.g. cationic-exchange resins and polymeric absorbing resins) that are known to those skilled in the art. Such antibiotic absorbing agents have been shown to reduce the residual activity of common antibiotics over time durations between 0.5-2 hours.

As shown at step 104, the antibiotic absorbing agents are removed prior to obtaining the first and second aliquots, using methods such as centrifugation or filtration.

Figure 1D:
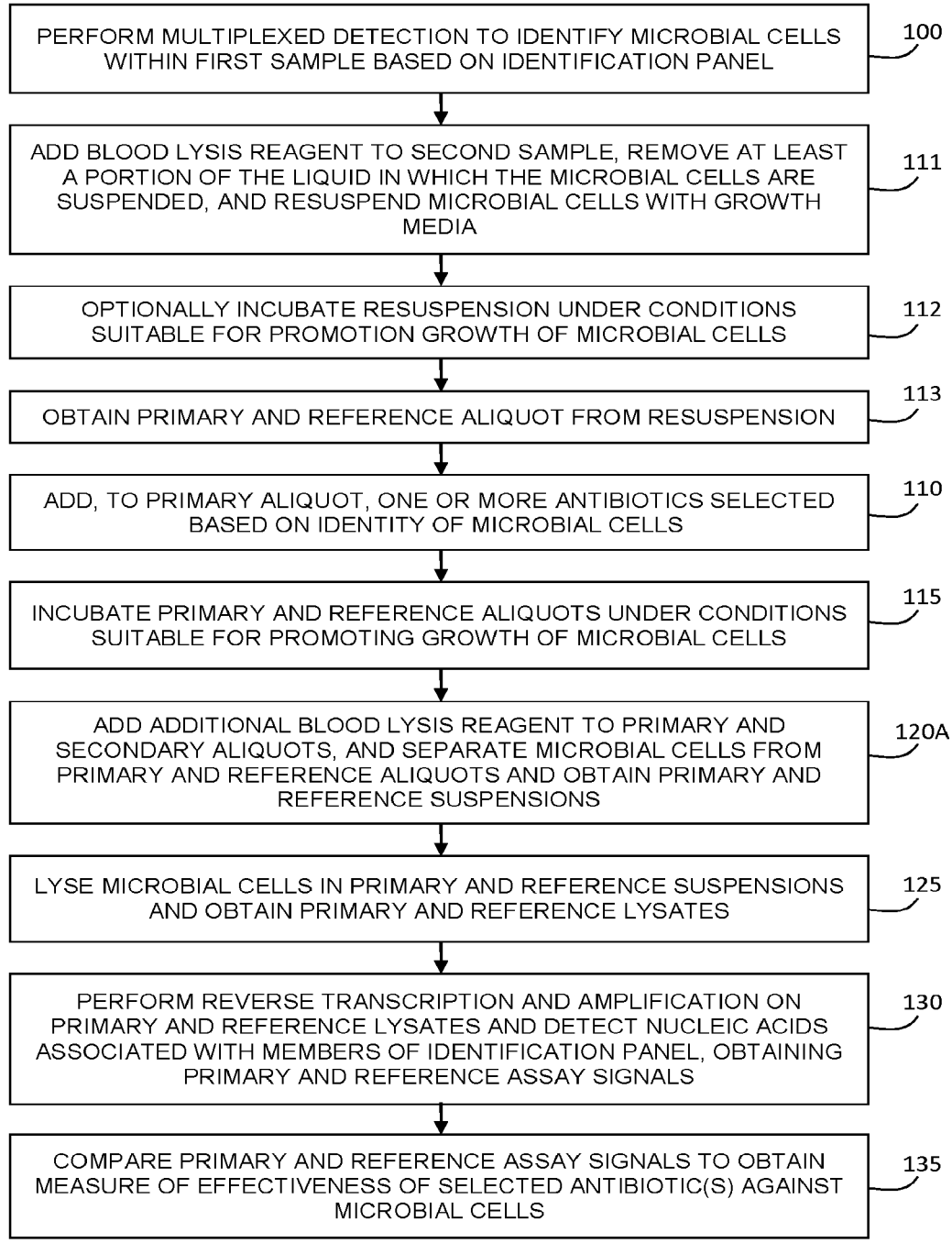
FIG. 1D is a flow chart illustrating an example implementation of a method for determining the antibiotic susceptibility of a whole blood sample, where at least a portion of the liquid in which the microbial cells are suspended is initially removed, to reduce the concentration of antibiotics initially present in the sample.

Referring now to FIG. 1D, an example method is described for determining the effectiveness of a selected antibiotic when the sample is a whole blood sample. After having performed the multiplexed panel of identification tests in step 111 (or alternatively, before this step), a blood lysis reagent is added to a second whole blood sample, in order to achieve lysis of at least some of the blood cells present in the sample.

After adding the blood lysis reagent and mixing the blood lysis reagent with the sample, at least a portion of the resulting mixture is removed, without removing while retaining the microbial cells. This may be achieved, for example, via filtration or centrifugation. For example, the mixture may be subjected to centrifugation, optionally in the presence of a cushioning liquid as described in US Patent Publication No. 2014/0154687, and at least a portion of the supernatant may be removed. For example, the portion of the supernatant that is removed may be between 50% and 75%, between 75% and 90%, between 90% and 95%, and more than 95%, according to different example implementations.

Following the removal step, growth media is added to the remaining suspension, such that the microbial cells are resuspended with growth media. Without intending to be limited by theory, it is suspected that the partial lysis of the blood cells improves the growth of the microbial cells in the sample. This resuspended sample may then be incubated under conditions suitable for promoting growth of the microbial cells as shown at step 112, for example, for a time duration between one and two hours, or, for example, between two and three hours. In one example implementation, a composition of the blood cell lysis reagent, per approximately 1 mL of whole blood, may be provided as follows: an aqueous solution having a volume of approximately 100 µL with a concentration of approximately 40 mg/mL saponin (84510, Sigma), approximately 10 mg/mL sodium polyanetholesulfonate (SPS) (P2008, Sigma) and approximately 1% by volume of poly(propylene glycol) (PPG) MW 2000 (202339, Sigma). Upon mixing the blood lysis reagent with the whole blood sample the final concentrations of Saponin, SPS and PPG are approximately 3.6 mg/ml, 0.9 mg/ml, and 0.09% respectively.

In one example implementation, the concentrations of saponin and SPS upon mixing whole blood and the blood lysis reagent may be in the range of approximately 1.0 to 10 mg/mL and 0.5 to 2 mg/mL, respectively.

In another example implementation, a composition of the blood cell lysis reagent, for lysing approximately 1 mL of whole blood, may be provided as follows: an aqueous solution having a volume of approximately 100 µL, with a concentration of approximately 1.5% by volume Triton X-100 (X-100, Sigma), approximately 18 mg/mL sodium polyanetholesulfonate (SPS) (P2008, Sigma) and approximately 1% by volume poly(propylene glycol) (PPG) MW 2000 (202339, Sigma) in a buffer pH ranging from 5 to 11. Upon mixing the blood lysis reagent with the whole blood sample the final concentrations of Triton X-100, SPS and PPG are approximately 0.14%, 0.55 mg/ml, and 0.03% respectively.

In one example implementation, the concentrations of Triton X-100 and SPS upon mixing the lysing reagent and whole blood sample may be in the range of approximately 0.05 to 0.5% and 0.2 to 2 mg/mL, respectively. As noted above, the initial exposure to the blood lysis reagent and subsequent removal of at least a portion of mixture (while retaining the microbial cells), may be beneficial in promoting growth without significantly compromising the viability of the microbial cells, and may also be beneficial in concentrating the remaining suspension. Furthermore, the amount of the mixture that is removed, and the amount of growth media that is subsequently added, may be employed to achieve a dilution of antibiotics that were present in the sample at the time of sampling (for example, achieving at least a 50%, 75%, 90% or 95% dilution of an undesired antibiotic).

After having performing the initial blood lysis step, the aliquots are obtained and incubated as described previously, according to steps 113 to 115.

The microbial cells in the primary and reference aliquots may then be separated, where a blood lysis reagent is added to each aliquot prior to the separation step, in order to achieve lysis of at least some of the blood cells that may still be present in the aliquots. For example, the blood lysis reagent may be provided as described in US Patent Publication No. 2014/0154687. For example, For example, in one example implementation, a composition of the blood cell lysis reagent, per approximately 1 mL of whole blood, may be provided as follows: an aqueous solution having a volume of approximately 500 µL with a concentration of approximately 75 mg/mL saponin (84510, Sigma), approximately 15 mg/mL sodium polyanetholesulfonate (SPS) (P2008, Sigma) and approximately 1% by volume of poly(propylene glycol) (PPG) MW 2000 (202339, Sigma). Upon mixing the blood lysis reagent with the whole blood sample the final concentrations of Saponin, SPS and PPG are approximately 25 mg/ml, 5 mg/ml, and 0.3% respectively.

In one example implementation, the concentrations of saponin and SPS upon mixing whole blood and the blood lysis reagent may be in the range of approximately 1.5 to 80 mg/mL and 0.5 to 20 mg/mL, respectively. In another example implementation, the concentrations of the saponin and SPS may be in the range of from approximately 10 to 30 mg/mL and 2.5 to 10 mg/mL, respectively.

In another example implementation, a composition of the blood cell lysis reagent, for lysing approximately 1 mL of whole blood, may be provided as follows: an aqueous solution having a volume of approximately 500 µL, with a concentration of approximately 1.5% by volume Triton X-100 (X-100, Sigma), approximately 18 mg/mL sodium polyanetholesulfonate (SPS) (P2008, Sigma) and approximately 1% by volume poly(propylene glycol) (PPG) MW 2000 (202339, Sigma) in a buffer pH ranging from 5 to 11. Upon mixing the blood lysis reagent with the whole blood sample the final concentrations of Triton X-100, SPS and PPG are approximately 0.5%, 6 mg/ml, and 0.3% respectively. In one example implementation, the concentrations of Triton X-100 and SPS upon mixing the lysing reagent and whole blood sample may be in the range of approximately 0.1 to 1.5% and 1 to 10 mg/mL, respectively.

After having added the blood lysis reagent, the microbial cells may be separated using a method such as filtration or centrifugation. For example, the microbial cells may be separated via centrifugation, with optional washing, as per the methods disclosed in US Patent Publication No. 2014/

0154687. The separated microbial cells may then by lysed and assayed as described above, according to steps 125 to 135.

Figure 1E:
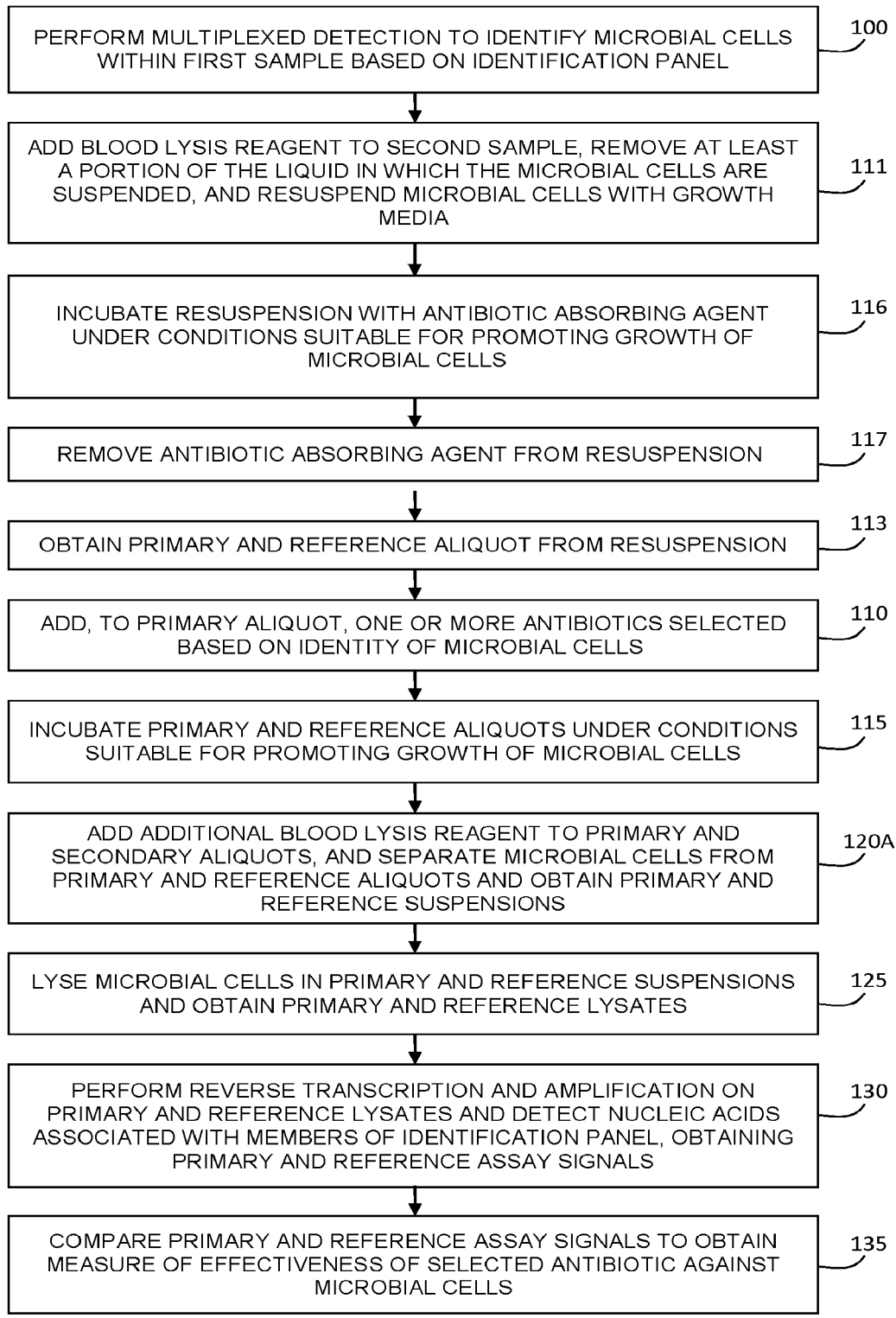
FIG. 1E is a flow chart illustrating an example implementation of a method for determining the antibiotic susceptibility of a whole blood sample, where the sample, upon which antibiotic sensitivity testing is performed, is initially pre-incubated with antibiotic absorbing agents to remove antibiotics initially present in the sample.

As shown in FIG. 1E, additional steps may be provided to achieve further reduction in the presence of, or activity of, antibiotics that were present in the sample at the time of sampling. For example, as shown at steps 116 and 117, the antibiotic absorbing agents may be added, and subsequently removed from the suspension of microbial cells, in a manner similar to that described above in association with FIG. 1C.

The aforementioned example embodiments may be beneficial in addresses issues with sampling as follows. The separation step may employ centrifugal concentration (or concentration via filtration and subsequent resuspension) of microbial cells, such that sufficient volume of raw sample can be used without being limited with the constraints imposed by the sample size in next stages. For instance, smaller sample sizes of order 1 mL or less are desirable for automating the assay steps, while lowering detection limit to about 1 CFU/mL requires samples with volumes much larger than 1 mL. Secondly, the pre-incubation of the second sample (and/or aliquots) with growth media allows for increase in the number of microbial cells, thereby reducing the sensitivity of the system to statistical sampling errors. Thirdly, the multiplexed identification test panel that is performed prior to antibiotic susceptibility testing generally limits to number of candidate antibiotics to a low number, such as one, two, or three candidate antibiotics (as per the antibiogram of the treatment facility). In addition, the number of relevant antibiotic test concentrations may be reduced to one concentration, or perhaps two or three, concentration, when the antibiogram of the treatment facility is taken into account. Fourthly, employing RNA as the detection target minimizes post-lysis sampling errors due to high copy number of RNA molecules. As disclosed herein, the target RNA molecules selected for nucleic acid amplification detection may be chosen to be ribosomal RNA (rRNA), transfer messenger RNA (tmRNA) or abundant messenger RNA.

Figure 2A:
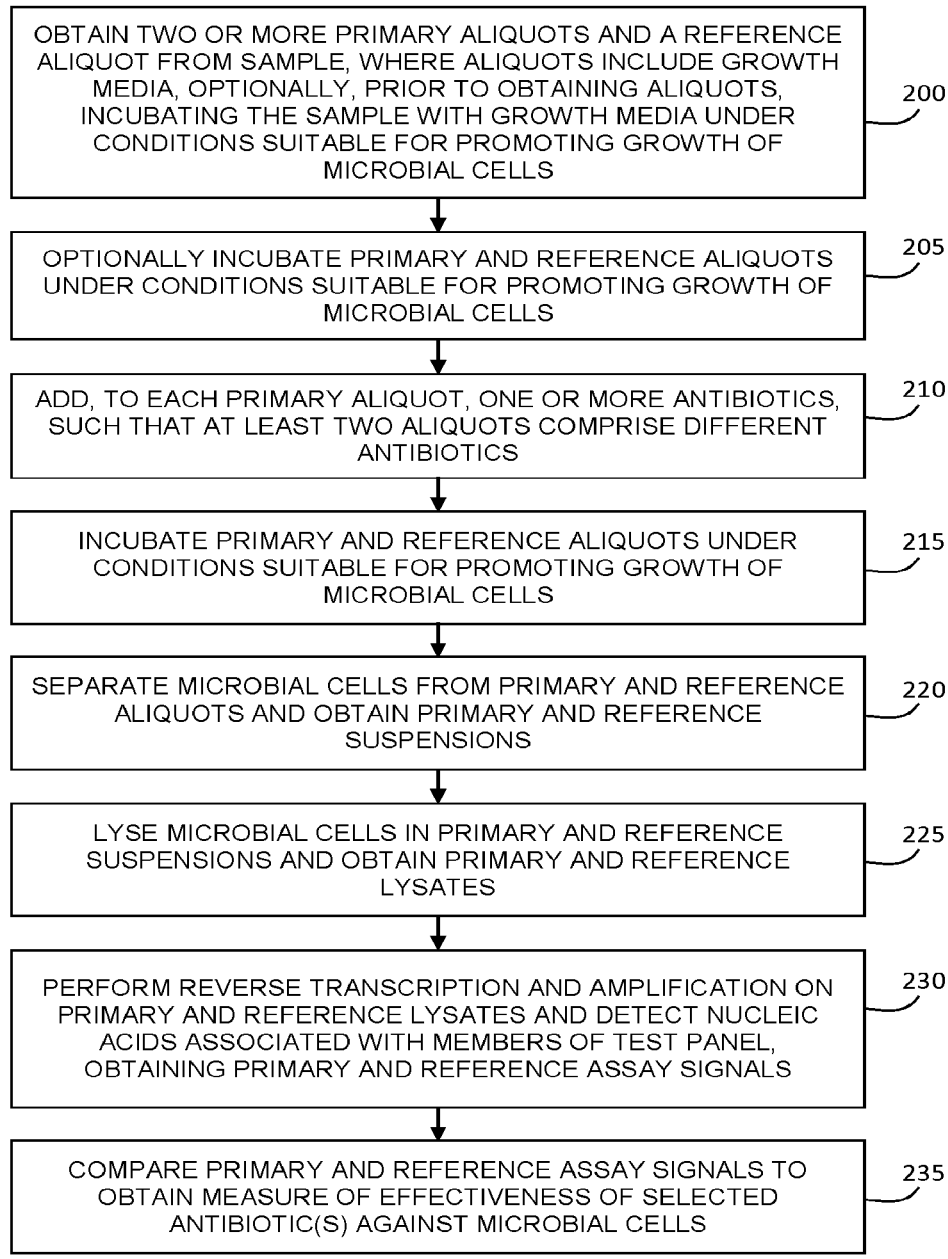
FIG. 2A is a flow chart illustrating an example implementation of a method for determining the antibiotic susceptibility of microbial cells in a sample, where a sample aliquot is incubated in the presence of one or more antibiotics and growth media, and where the microbial cells are subsequently separated, lysed, and subjected to reverse transcription and amplification. The effectiveness of the antibiotic(s) is determined by comparing the assay signal to a reference assay signal obtained from a reference aliquot.

FIG. 2A illustrates an example embodiment in which antibiotic susceptibility testing is performed without requiring the performing of an initial multiplexed identification test panel. As shown at step 200, two or more primary aliquots are obtained from a sample, and at least one reference sample is also obtained. The initial sample may optionally be initially incubated with growth media prior to obtaining the aliquots, or the aliquots may optionally be incubated with growth media, as shown at step 205 in order to increase the number of microbial cells present in the aliquots.

In step 210, one or more antibiotics are added to each primary aliquot, such that at least two of the primary aliquots include different antibiotics. Accordingly, the primary aliquots are tested for a panel of different antibiotics, and where two or more primary aliquots may include different concentrations of the same antibiotic. Steps 215 to 225 are performed as described in steps 115 to 125 of FIG. 1A, in order to process the aliquots and obtain lysates from each aliquot.

In step 230, reverse transcription and amplification is performed on the primary and secondary lysates in order to detect RNA-based nucleic acid sequences that are associated with the presence of microbial cells from a test panel. For example, the test panel may be a set of clinically relevant Gram-positive, Gram-negative, and fungal microbial cells. The nucleic acid sequences that are detected are either a collection of nucleic acid sequences from members of the test panel may include one or more sequences specific to the microbial cell types making up the test panel. One or more of the nucleic acid sequences that are detected may include a sequence that is conserved among two or more members of the test panel. The resulting assay signals from the primary lysates and the secondary lysates are then compared to determine the effectiveness of the antibiotics, without having identified the microbial cells present in the sample. Such an embodiment may be useful when initial antibiotic effectiveness information is needed with urgency, as it does not require waiting for the performance of the initial multiplexed identification test panel.

Figure 2B:
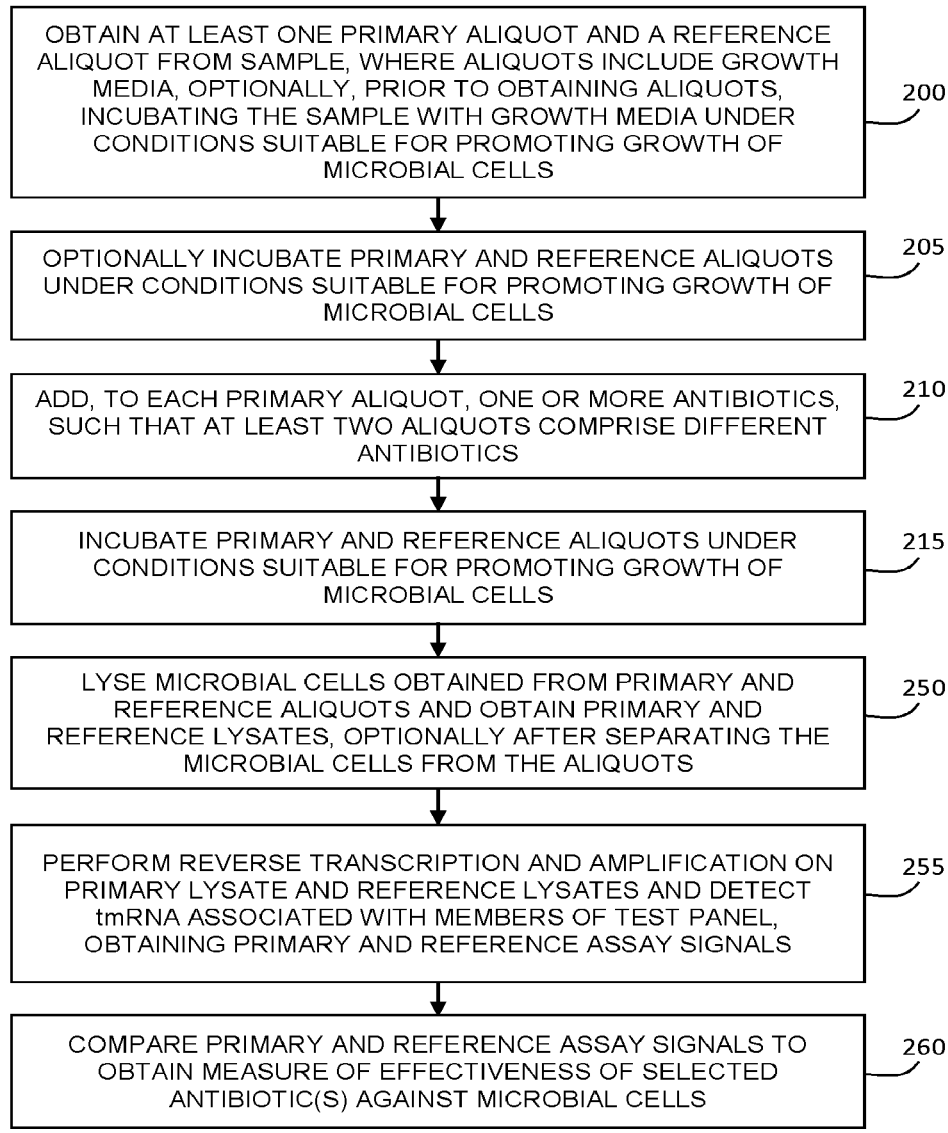
FIG. 2B is a flow chart illustrating an example implementation of a method for determining the antibiotic susceptibility of microbial cells in a sample, where a sample aliquot is incubated in the presence of one or more antibiotics and growth media, and where the microbial cells are subsequently lysed and subjected to reverse transcription and amplification to detect transfer messenger RNA (tmRNA). The effectiveness of the antibiotic(s) is determined by comparing the assay signal to a reference assay signal obtained from a reference aliquot.

FIG. 2B illustrates an example method of performing antibiotic susceptibility testing via reverse transcription and amplification for the detection of tmRNA, where the method may be performed with or without initial identification of the microbial cells via a multiplexed identification test panel. The steps followed in FIG. 2B are similar to those disclosed in FIG. 2A. In step 255, reverse transcription is performed on the primary lysate and the reference lysate in order to detect tmRNA that is associated with microbial cells belonging to a test panel. In step 260, the primary and reference assay signals are then compared in order to determine the effectiveness of the selected antibiotic.

Figure 2C:
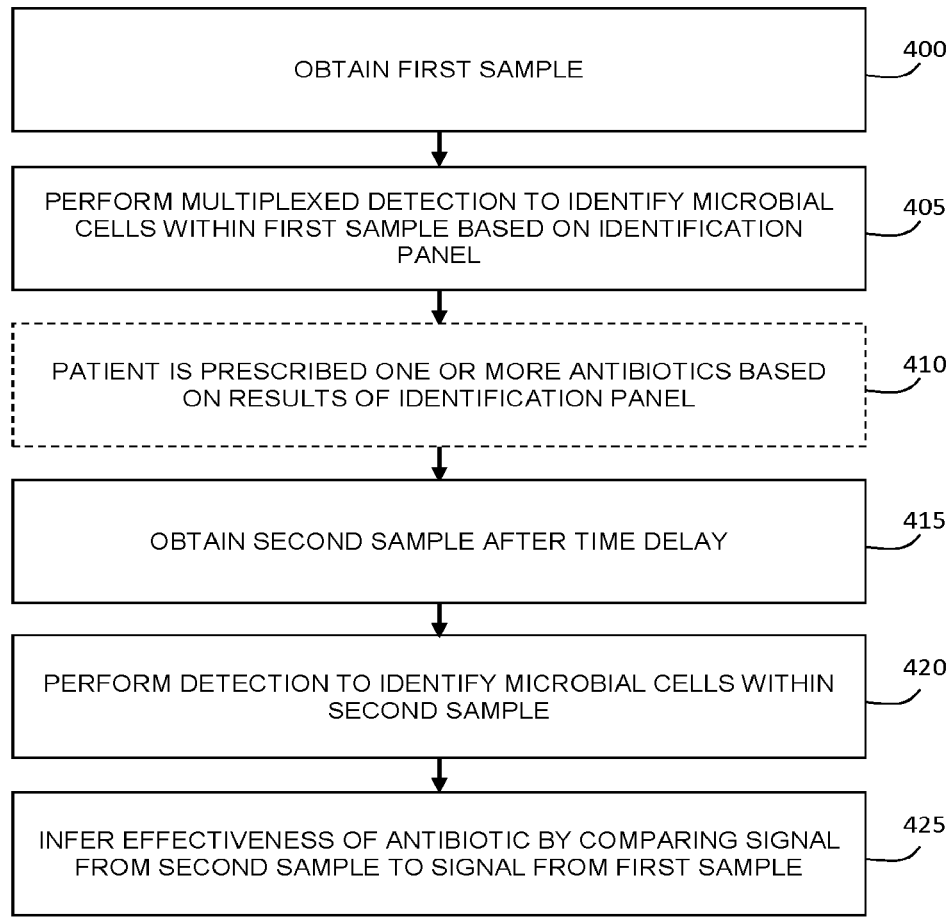
FIG. 2C is a flow chart illustrating an example method of performing antibiotic susceptibility testing based on the in-vivo exposure of microbial cells to one or more antibiotics.

FIG. 2C illustrates an alternative example embodiment in which antibiotic susceptibility testing is performed based on the in-vivo exposure of the microbial cells to a prescribed antibiotic. In step 400, a first sample is obtained from a patient or subject, where the sample is suspected of containing microbial cells. A rapid multiplexed identification test panel is then performed to obtain information pertaining to the identity of the microbial cells, as described above. For example, the sample preparation, separation, and lysis methods disclosed in US Patent Publication No. 2014/0154687 and US Patent Publication No. 2014/0004501 may be employed.

In step 410, one or more antibiotics are selected based on the results from the identification panel. For example, any of the aforementioned methods of selection of an antibiotic may be employed.

After the one or more antibiotics have been prescribed to the patient or subject, and after an in-vivo incubation delay has elapsed (e.g. a time delay of less than one hour, between one hour and two hours, between two hours and three hours, between three hours and four hours, or more than four hours), a second sample is obtained at step 415.

The second sample is then tested, at step 420, to determine the change in the assay signal due to the in-vivo incubation of the microbial cells with the antibiotics prescribed to the patient. This test may be the same multiplexed identification test panel. In another embodiment, the test panel may be a subset of the original identification test panel, based on one or more of the tests that were positive when the first sample was tested. Finally, at step 425, the assay signals from the first and second tests are compared in order to determine whether or not the prescribed antibiotic(s) were effective against the microbial cells.

In other example embodiments described below, methods for probing the mRNA content of a cell on a rapid timescale for the determination or estimation of antibiotic susceptibility of microbial cells. The example embodiments described below provide methods involving the estimation or determination of the susceptibility level of microbial cells to an antibiotic based on the transcriptional status (e.g. the quantity or concentration) of a target mRNA produced in response to a stimulus. Unlike known methods of antibiotic susceptibility testing, embodiments of the present disclosure support the determination of susceptibility or resistance directly from patient samples in a short period, thereby meaningfully impacting the treatment options.

According to some embodiments, antibiotic susceptibility testing may be performed after having first obtained information associated with the identify of microbial cells within a sample (e.g. the genus, species, kingdom, Gram stain status, or another identifying characteristic, such as a molecular sequence belonging to DNA or RNA of the microbial cell), such that one or more candidate antibiotics may be selected (as described above). The microbial cells are then subjected to the selected antibiotic, (e.g. a suspension is provided including the microbial cells and the antibiotic, such as a blood sample or a liquid blood culture media), and incubated under conditions that would support growth of the microbial cells in the absence of the antibiotic (and optionally in the presence of the antibiotic, for example, in the case of resistant microbial cells). The microbial cells are incubated with the antibiotic for a time duration that is sufficiently long for the antibiotic to induce, in susceptible and/or resistant microbial cells, a response, such as a transcriptional, phenotypic or metabolic response (for example, from approximately half an hour, to approximately two hours). After having subjected the microbial cells to the antibiotic, the microbial cells are lysed to release target mRNA, which is subsequently detected in order to assess the susceptibility of the microbial cells to the antibiotic.

Unlike known methods of antibiotic susceptibility testing, the induced response of the microbial cells to the antibiotic need not involve cell death or absence of cell growth, but may involve a response that is indicative of the long-term viability of the microbial cells following the exposure to the antibiotic. For example, the response of the microbial cells to the antibiotic may involve a metabolic change associated with a loss of long-term viability, such as the inhibition or suppression of the ability of the microbial cells to reproduce, and/or express a given mRNA in response to a stimulus.

In some embodiments, a target mRNA may be selected, for a given organism and antibiotic, such that the production of the mRNA within the cells is directly associated with the resistance and/or susceptibility of the microbial cells to the antibiotic, and where the exposure of the microbial cells to the antibiotic produces a rapid modification in the intracellular concentration of the target mRNA.

The target mRNA may be selected such that the induced production of the intracellular mRNA occurs within seconds or minutes of exposure to the antibiotic. For example, the microbial cells may be resistant to the antibiotic, and the response of the microbial cells to exposure to the antibiotic may involve the production of target mRNA to support the viability of the microbial cells under exposure to the antibiotic. Such target mRNA may be detected to determine the resistant nature of the microbial cells. In another example, the microbial cells may be susceptible to the antibiotic, and the response of the microbial cells to exposure to the antibiotic may involve the production of target mRNA indicative of a reduction in the viability of the microbial cells under exposure to the antibiotic. Such target mRNA may be detected to determine the susceptible nature of the microbial cells.

The microbial cells may be lysed to release the target mRNA, such that the target mRNA remains stable in the lysate, and an assay may be performed to determine a measure associated with the presence of, or the quantity of, the mRNA in the lysate. The lysis and mRNA assay may also be performed on a sample aliquot that had not been exposed to the antibiotic, and the measures obtained from the two aliquots may be compared to determine or estimate the susceptibility of the microbial cells to the antibiotic.

In other embodiments, a target mRNA may be selected such that its production is indirectly related to the exposure of the microbial cells to the antibiotic. The stimulus and target mRNA are selected such that the production of mRNA for susceptible and/or resistant microbial cells is altered due to exposure of the microbial cells to the antibiotic. For example, the target mRNA may be selected to be mRNA that are produced by viable cells (or, for example, cells in a growth phase) in response to the stimulus, such that the production of target mRNA in susceptible microbial cells is reduced after exposure to the antibiotic, and the production of target mRNA is substantially unchanged in resistant microbial cells. According to such an embodiment, after having exposed the microbial cells to the antibiotic for a time duration that is sufficiently long for susceptible and/or resistant microbial cells to undergo a phenotypic, metabolic, or other response to the presence of the antibiotic, the microbial cells may be subjected to the stimulus associated with the production of a target mRNA in the microbial cells.

The microbial cells may then be rapidly lysed to release the target mRNA, such that the target mRNA remain stable in the lysate (i.e. the target mRNA does not substantially degrade within the lysate upon lysis), and an assay may be performed to determine a measure associated with the presence of, or quantity of, target mRNA in the lysate. The stimulus, lysis and mRNA assay may also be performed on an aliquot that had not been exposed to the antibiotic, and the measures obtained from the two aliquots may be compared to determine or estimate the susceptibility of the microbial cells to the antibiotic.

As noted above, the target mRNA is released in a detectable form by performing rapid cell lysis in a manner that renders the target mRNA in a substantially stable form, such that the target mRNA may be subsequently detected without significant degradation. The production of mRNA in response to the presence of the antibiotic or stimulus can occur on a rapid timescale, such a timescale of seconds or minutes. Accordingly, in some embodiments, the lysis of the microbial cells is performed within a time duration associated with the production of the target mRNA within the microbial cells (e.g. on a timescale associated with the lifetime of target mRNA produced within the microbial cells, for example within approximately 30 seconds to ten minutes), such that the mRNA released and detected is indicative of the response of the microbial cells to the presence of the antibiotic or the application of the stimulus.

It will be appreciated by those skilled in the art that many conventional lysis methods will not be capable of meeting the dual constraints of (a) performing lysis within a time duration associated with the production of the target mRNA within the microbial cells in response to the antibiotic or applied stimulus, and (b) producing a lysate in which the target mRNA is stable.

One example lysis method may involve removal of the potential PCR inhibitors and nucleases in the cell suspension followed by performing a rapid lysis protocol, such as bead beating with or without ultrasonic irradiation, in a lysis buffer that may include nuclease inhibitors. Unfortunately, these methods involve multiple steps and reagents, and often require subsequent purification steps prior to performing PCR.

In one example implementation, the aforementioned dual lysis constraints may be satisfied by the rapid electrical lysis methods disclosed in US Patent Publication No. 2014/0004501. Such a method provides rapid electrical lysis on a timescale that is much less than the timescale of target mRNA production, and also provide a lysate that is suitable for maintaining the target mRNA in a stable form due to the inactivation of nucleases.

Figure 3:
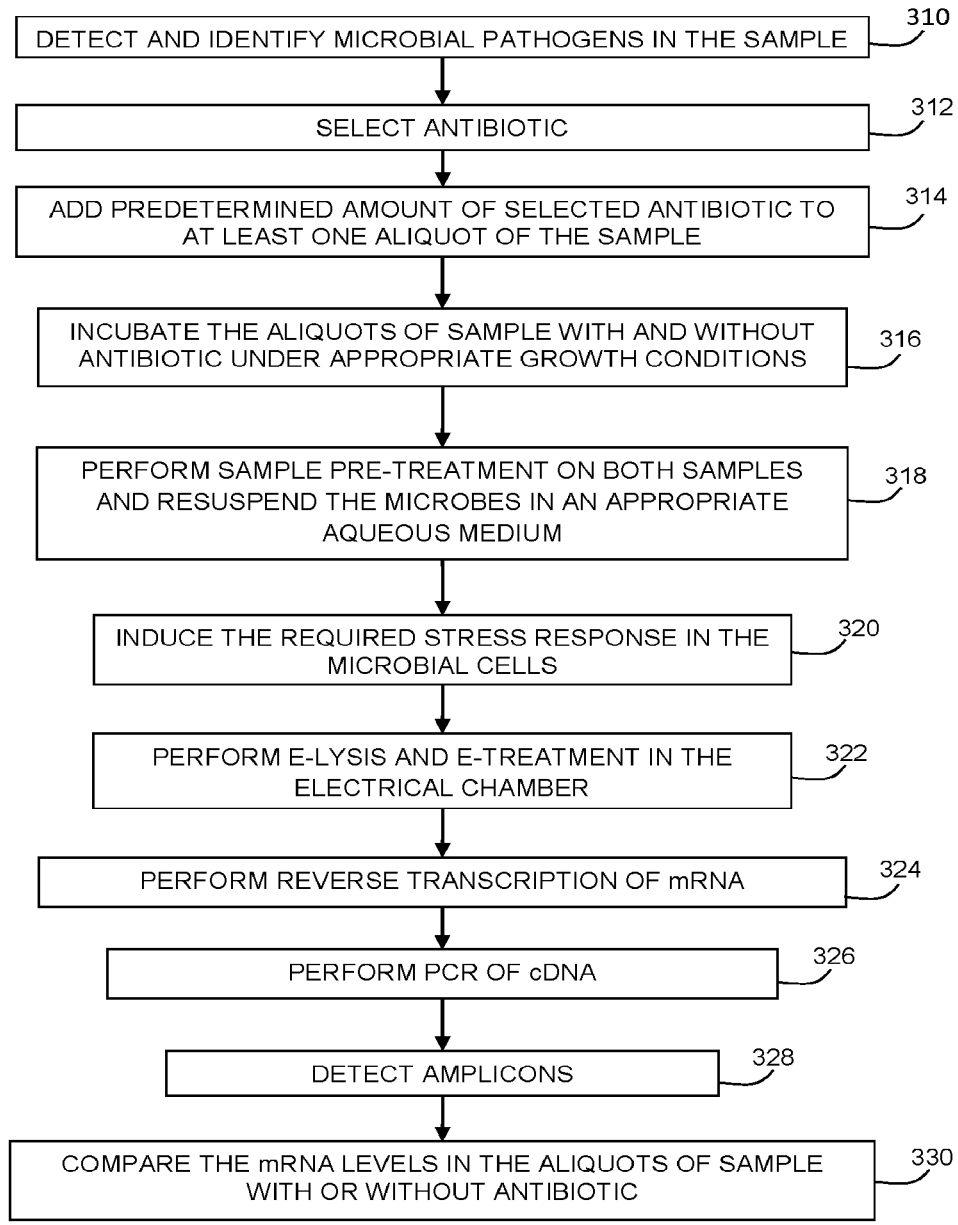
FIG. 3 provides a flow chart illustrating an example implementation of a rapid mRNA analysis method for determining the antibiotic susceptibility of microbial cells in a sample, where the production of mRNA is associated with a stimulus applied after exposure to the antibiotic.

Referring now to FIG. 3, a flow chart is provided that illustrates an example method of performing microbial susceptibility testing, according to one embodiment, in which an external stimulus is applied after having exposed microbial cells in a sample to an antibiotic, where the stimulus is provided to induce the production of mRNA within the microbial cells, and where the microbial cells are subsequently lysed for the assessment of antibiotic susceptibility based on the detection of the mRNA. In the present non-limiting example method, lysis is performed using the electrical lysis method disclosed in US Patent Publication No. 2014/0004501.

In step 310, the sample is tested for the presence and the identity of the pathogenic microbial cells. This step may be performed according to a wide variety of methods, where the selected method will depend on the nature of the sample. For example, if the sample is a positive blood culture sample, methods such as conventional phenotypic testing, fluorescence in-situ hybridization, and MALDI-based detection may be employed (in some cases, it may be necessary to first obtain an isolate via subculture). If the sample has not been subjected to culturing, direct sample identification may be performed using a molecular method such as the LightCycler® SeptiFast Test MGRADE, Sepsitest™, and YVOO® protocols. In another example implementation, the identification of the microbial cells may be performed according to the methods disclosed in US Patent Publication No. 2014/0154687, as described above.

The antibiotic selection is then made in step 312. The antibiotic selection may be made according to known methods, such as based on published or known antibiotics that have been shown to be effective against the identified microbial cells, and/or based on an antibiogram. Although the examples embodiments provided herein relate to the selection and testing of one antibiotic, it is to be understood that more than one antibiotic may be tested.

In step 314, at least two aliquots of the sample are obtained. A predetermined amount of the selected antibiotic may be determined, for example, according to known or standardized values, such as those quoted in the Clinical and Laboratory Standards Institute (CLSI) antimicrobial susceptibility testing standards. The antibiotic may be added to one aliquot, and at least one other aliquot is used as a control without antibiotic Although the example embodiments provided herein describe the testing of a single amount or concentration of a selected antibiotic, it is to be understood that multiple amounts or concentrations of the selected antibiotic may be tested (e.g. in series or in parallel). For example, the sample may be prepared in multiple aliquots such that at least one aliquot is provided for each antibiotic amount or concentration. Embodiments with multiple antibiotic concentrations may facilitate the measurement, determination or estimation of a minimum inhibitory concentration or other measure associated with the effectiveness of the antibiotic.

The sample aliquots are then incubated under conditions appropriate for microbial growth (i.e. such that microbial cells would grow in the absence of the antibiotic during incubation), as shown in step 316. For example, the microbial cells may be incubated, at a suitable temperature (e.g. 37° C.), in a culture medium suitable for growth (without media designed to inhibit the effect of the antibiotics). In another example, the microbial cells may be incubated, at a suitable temperature (e.g. 37° C.), in the sample as drawn, such as directly, in blood, optionally with the inclusion of suitable anti-clotting agents.

In some embodiments, the suitable time for exposure to the antibiotic may be based, at least in part, on respective doubling time of the microbial cells and mode of action of the antibiotics. For example, antimicrobial agents that interfere with cell wall synthesis block the synthesis of peptidoglycans and the mechanism of cell death is by cell lysis due to defective or weakened cell walls. Therefore, cell wall synthesis inhibitors are active only against growing bacteria. The cell death mechanism is not immediate and involves many active cellular processes. The antimicrobial agents that interfere with DNA synthesis, for instance, bind to DNA gyrase-DNA complex and interfere with the repair of broken DNA strands by DNA gyrase during DNA replication, leading to immediate bacteriostasis followed by cell death.

According to the present example method, each aliquot is processed in step 318 such that the microbial cells are separated and optionally concentrated in a lysis buffer, thereby obtaining a suspension of microbial cells for each aliquot. The separation method may be performed using any suitable protocol, such as the protocols disclosed in in US Patent Publication No. 2014/0154687.

It is to be understood that the present example method provides but one example implementation, and that other methods may be performed to separate and optionally concentrate the microbial cells.

In step 320, each suspension is subjected to a stimulus that is selected to induce the production of target mRNA within the microbial cells. The target mRNA and the stimulus may be selected such that the production of the mRNA, in response to the stimulus, is altered due to the exposure to the antibiotic. For example, the target mRNA may be selected to be an mRNA that is produced by viable cells in response to the stimulus, such that the production of target mRNA in susceptible microbial cells is reduced after exposure to the antibiotic, and the production of target mRNA is substantially unchanged in resistant microbial cells. The stimulus may be any stimulus, such as a physical, chemical, or electrical stimulus, that causes the production of target mRNA. Examples of target mRNA and associated stimuli are provided below.

Electrical processing of each suspension is then performed in step 322, according to the methods described in US Patent Publication No. 2014/0004501, as described above. The electrical processing method lyses the microbial cells, and also renders the intracellular rRNA and genomic DNA accessible for external enzyme action. As noted above, the electrical processing method also provides electrical treatment in this step also substantially inactivates enzymes or factors inhibitory to subsequent amplification and detection.

In step 324, the lysate is mixed with an appropriate master mix, and reverse transcription is performed to transcribe mRNA in the lysate into corresponding cDNA. The master mix may contain components for performing cycles of PCR amplification on the cDNA. Amplification of the transcribed cDNA is then preformed via an amplification method, such as PCR (or variations thereof). Finally, the amplicons are detected in step 328 and their levels, corresponding to the two aliquots, are compared in step 330 to judge the susceptibility of the antibiotic.

The mRNA amplification and detection may be performed without removing the corresponding gDNA. In one embodiment, this may be achieved using a primer that binds specifically at low temperatures (RT temperatures range from 40-50° C.) and includes a non-specific DNA tag. This ensure that only mRNA is tagged by this primer, which can be subsequently used during PCR step (at high annealing temperatures) to specifically amplify the cDNA converted from mRNA in the previous reverse transcription (RT) step.

Figure 4A:
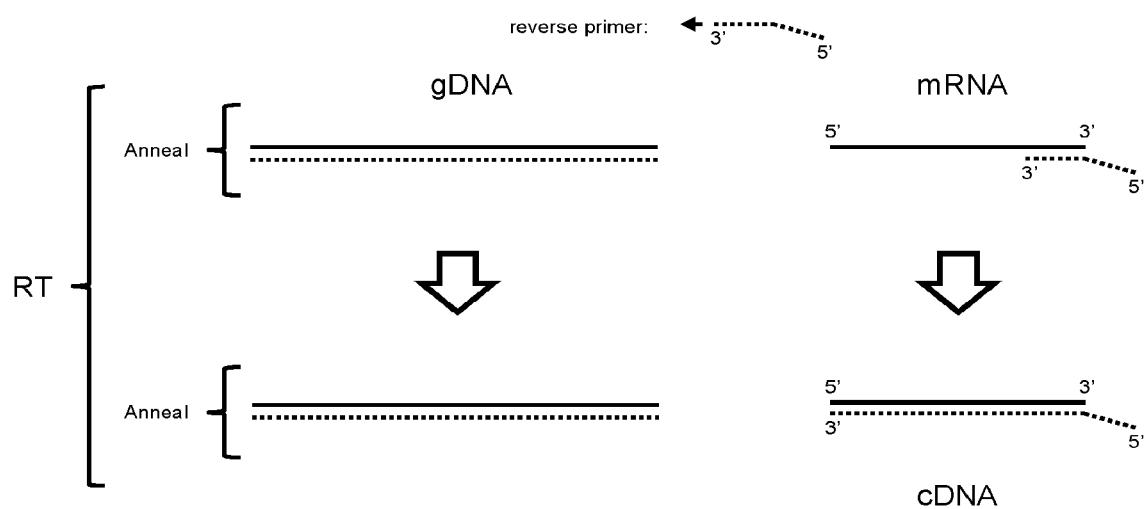
FIGS. 4A and 4B schematically describe the method of preferentially amplifying mRNA in the presence of the corresponding genomic DNA (gDNA).
Figure 4B:
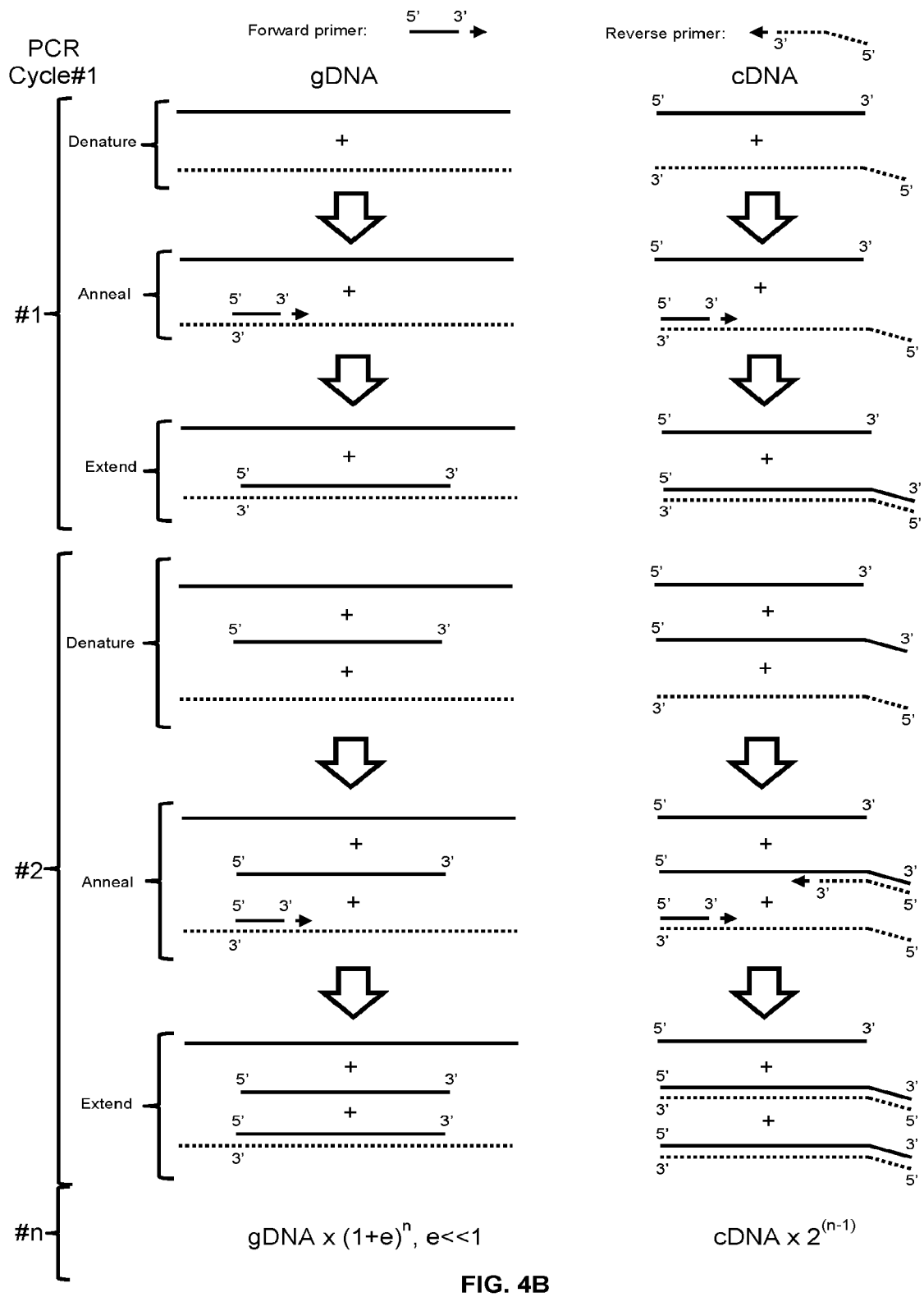
Figures 6, 7:
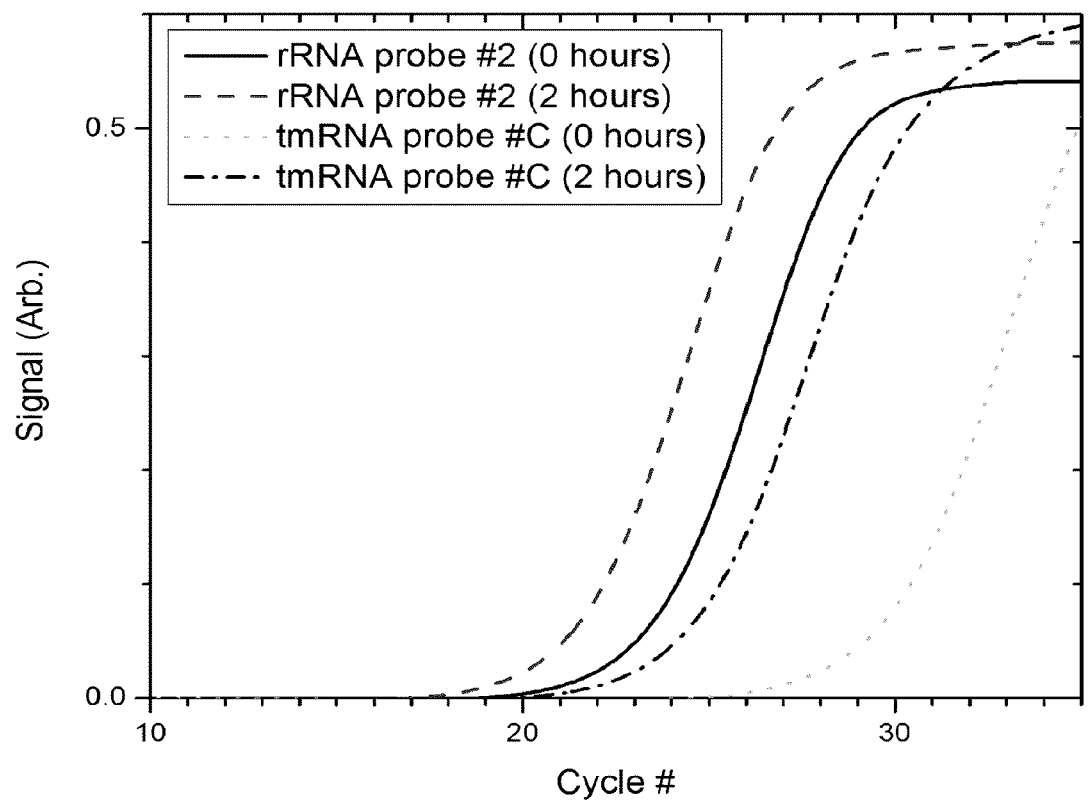
FIG. 6 plots the real time reverse transcription PCR (real-time RT-PCR) signals of *K. pneumoniae* ribosomal RNA (rRNA) and tmRNA detection obtained by processing a whole blood sample, the method involving lysis of blood cells and the addition of growth media, and subsequent pre-incubation for 2 hours.
FIG. 7 shows a table of the real time RT-PCR Ct values of *K. pneumoniae* rRNA and tmRNA obtained by processing a whole blood sample, the method involving lysis of blood cells and the addition of growth media, and subsequent pre-incubation for 2 hours.

The principle of the method can be understood by referring to FIGS. 4A and 4B. An example method for providing appropriate primers and performing an effective assay are as follows.

Initially, a forward and reverse primer are designed targeting the gene of interest. Remove nucleotides from the reverse primer (also the RT primer) until the melting temperature is in the low 40s. A non-specific DNA tag is then attached to the 5' end of the reverse primer. The melting temperature of the specific sequence+TAG should be greater than approximately 640° C. The RT reaction is then performed at approximately 42° C., and the PCR is performed with an annealing temperature of approximately 65° C. Under these conditions, amplification should only occur on the tagged cDNA (the cDNA obtained by the RT of mRNA with tagged reverse primers).

In FIG. 4A, reverse transcription (RT) is performed at low temperature (in the low 40° C.s) during which gDNA is not denatured for the tagged reverse primer annealing. Therefore, only mRNA is annealed by tagged reverse primers and reverse transcribed into tagged cDNA. During PCR Cycle #1 in FIG. 4B, the antisense strand of gDNA and the tagged cDNA are annealed by the forward primers and the respective sense strands are copied. The copied sense strand of gDNA is without the complementary sequences for the tag while the copied sense strand of tagged cDNA is with the complementary sequences for the tag. During PCR Cycle #2 in FIG. 4B, due to the presence of tag sequences in tagged nucleic acids only and high annealing temperature (greater than approximately 64° C.) of the tagged reverse primers, only the tagged reverse primers can successfully anneal to the tagged sense strand. During the following PCR cycles in FIG. 4B the tagged nucleic acids are exponentially amplified.

In the method and embodiments disclosed, any or all of the steps may be performed in an automated system in order to prevent contamination and reduce losses in the number of target mRNA molecules. The automation also reduces the time delay between processing steps and may be employed to increase or maximize "real-time" or snapshot nature of the mRNA detection.

As noted above, a wide variety of mRNA may be investigated according to the antibiotic susceptibility testing methods disclosed herein. For example, target mRNA may be selected that is produced in response to a stimulus by viable microbial cells (e.g. cells in a growth phase). In another example, target mRNA may be selected that is produced, in response to a specific antibiotic (e.g. formation of double-stranded DNA breaks by DNA synthesis inhibiting antimicrobial agents induce expression of SOS response genes such as DNA repair enzymes). The target mRNA may alternatively be selected by identifying a conserved bacterial death pathway which is a common mechanism of cell death by all bactericidal antibiotics (e.g. reactive oxygen species (ROS) generation, which should be activated in susceptible bacterial strains).

Non-limiting examples of target mRNA and its associated genes for detection include the following. With regard to monitoring the growth of bacteria, numerous genes are associated with bacterial division and growth (for example, DnaK, TufA, RpoA). By monitoring the mRNA levels of these genes (with or without the application of a stimulus), it is possible to determine whether bacteria are growing in the presence of an antibiotic.

Other example genes and target mRNA are associated with highly orchestrated bacterial responses to environmental stresses such as heat shock, cold shock, nutrient limitation (stringent response) and DNA-damaging agents (SOS response). Example genes and target mRNA associated with heat shock are heat shock proteins (hsp), Example genes and target mRNA associated with cold shock are cold shock proteins (csp). Example genes and target mRNA associated with stringent response to mupirocin which is isoleucyl tRNA synthetase inhibitor are enzymes involved in isoleucine biosynthesis (ilv, leu). Example genes and target mRNA associated with SOS response to mitomycin C are proteins involved in DNA metabolism (uvr, ssb). In another example, some specific genes and target mRNA can be induced in the presence of specific small molecules. For example, induction of the enzymes involved in lactose fermentation; Lac operon genes, by isopropyl-(3-D-thiogalactoside (IPTG). The ability of antibiotic-susceptible microbial cells to respond to these inducers may be inhibited, and this mechanism could be used, for example, to determine whether a bacterial strain is resistant to specific antibiotics.

Furthermore, bacterial apoptotic-like pathways have recently been characterized and may be applicable to determining whether bacteria are being killed by a specific antibiotic. It is believed that many antibiotics act through reactive oxygen species (ROS) generation, which may be another method to determine susceptibility of microbial cells to antibiotics.

The half-lives of most bacterial mRNAs range from 40 s to 60 min, depending on variation in the stability of transcripts. For example, the majority of mRNA half-lives of transcripts produced in *Staphylococcus aureus* are rapidly degraded (89.7% had less than 5 min) while 1.1% of transcripts were stable (half-lives of >30 min). Interestingly, the induction of heal shock and cold chock responses in these bacteria appeared to dramatically stabilize mRNA transcripts, with the majority of them having half-lives of between 5 and 30 min. (Anderson et al., J Bacterial 2006 188 (19):6739).

While the preceding embodiments have disclosed methods of targeted antibiotic susceptibility testing, is to be understood that methods disclosed herein may be modified and/or adapted to be useful for other applications. For example, in one example implementation, the aforementioned method embodiments may be modified to assess, investigate, or determine the state of one or more microbial cells by detecting target mRNA that is produced in response to a stimulus. For example, the viability of one or more cells may be assessed by providing a stimulus to a suspension containing microbial cells, where the stimulus is selected to induce mRNA production in viable microbial cells, lysing the microbial cells within a timescale associated with the production of mRNA within the microbial cells, and detecting the mRNA in the lysate. It will be understood that such embodiments may be employed for a wide range of applications, including, but not limited to, clinical diagnostics, epidemiological studies, forensics, development of antimicrobial agents, and high-throughput screening of therapeutic candidates.

The following examples are presented to enable those skilled in the art to understand and to practice embodiments of the present disclosure. They should not be considered as a limitation on the scope of the disclosure, but merely as being illustrative and representative thereof.

EXAMPLES

In examples 1 and 2, Gram-negative *Escherichia coli* and *Klebsiella pneumoniae* bacteria cells were grown on LB agar plates and a single colony of cells was cultured in LB broth overnight at 37° C. The cells were centrifuged at 7000 rpm for 5 min. The cell pellet was washed twice and re-suspended in 0.8 mM phosphate buffer pH 7.4, pre-filtered through a 0.2 µm filter.

The blood cell lysis reagent was used whenever blood sample pretreatment was required. The blood cell lysis reagent consisted of a mixture of saponin (84510, Sigma), sodium polyanethol sulfanate (SPS) (P2008, Sigma) and poly(propylene glycol) (PPG) MW 2000 (202339, Sigma). Saponin was dissolved in reagent grade water, filtered through 0.2 µm PES syringe filter and purified using Amicon Ultra-15 10K MW cut-off (Z706345, Sigma). SPS was dissolved in reagent water and filtered through 0.2 µm PES syringe filter. PPG MW 2000 (202339, Sigma) was used directly from the original bottle. In addition, Fluorinert™ FC-40 (F9755, Sigma) was added to serve as cushioning liquid.

Unless any variation is specified, the following example pretreatment procedure which includes blood cell lysis step followed by 4 wash cycles was performed in experiments which required pretreatment of blood samples. 10 µL of Fluorinert™ was added to 2 mL siliconized microcentrifuge tubes (T3531, Sigma), followed by the addition of 500 µL of the blood cell lysis reagent. The blood cell lysis reagent consisted of 75 mg/mL saponin, 15 mg/mL SPS and 1% PPG. EDTA-treated human whole blood from healthy volunteers of 1 mL spiked with microbial cells was added to the tube containing the blood cell lysis reagent and the Fluorinert™, and mixed by inverting ten times and vortexing at low speeds for 10 sec. The final concentrations of the components in the mixture were 25 mg/mL saponin, 5 mg/mL SPS and 0.33% PPG. The tubes were centrifuged at 12,000 rpm for 1 min and 1.35 mL of the supernatant was removed, leaving 150 uL of the liquid supernatant, Fluorinert™ and the sedimented microbial I cells. The first wash cycles was performed by adding 1.35 mL of 0.8 mM phosphate buffer to the remaining liquid supernatant of 150 uL as described above, mixing by vortexing at low speed for 10 sec, centrifugation at 12,000 rpm for 1 min and removal of 1.35 mL of the supernatant, leaving 150 µL of the liquid supernatant, the Fluorinert™ and the sedimented microbial. The remaining wash cycles were performed by adding 0.75 mL of 0.8 mM phosphate buffer to the remaining liquid supernatant of 150 uL, mixing by vortexing at low speed for 10 sec, centrifugation at 12,000 rpm for 1 min and removal of 0.75 mL of the supernatant, leaving 150 µL of the liquid supernatant, the Fluorinert™ and the sedimented microbial. After the last wash, the sedimented microbial cells were re-suspended in the residual liquid. Positive control samples are prepared by spiking 0.8 mM phosphate buffer pH 7.4 with the same concentration of respective microbial cells as the nominal concentration of the pretreated sample in respective experiments.

In examples that employed electrical cell lysis, the pretreated samples and the positive control samples were passed through an electrical chamber with steps of 10 µL/10 s and applying n=250 bipolar square pulses having duration of 50 µs and amplitude of 190 V. The electrical chamber had a dimension of 6.4×15×0.2 $mm^3$ and the inlet and outlet ports were of restricted type.

In the following examples, real-time reverse transcription PCR (real-time RT-PCR) assay was performed to detect a specific target region in 16S rRNA, tmRNA or mRNA of respective microbial cell types. The primers were designed by sequence alignment software (Bioedit, Ibis Biosciences, USA) and primer design software (Primer3, National Institutes of Health). The cell lysate of the pretreated sample following the electrical lysis was subjected to real-time RT-PCR.

Unless any variation was specified, RT-PCR reaction of 5 µL volume was prepared by mixing 1 µL of sample, 1 µL of Kapa 2G Robust Hotstart 5× buffer (KK5517, KAPA Biosystems), 0.05 µL of Kapa 2G Robust Hotstart DNA polymerase (kk5517, KAPA Biosystems), 0.2 µL of reverse transcriptase (GoScript, A5004 Promega), 0.04 uL of 100 mM dNTPs (10297-117, Life Technologies), 0.25 uL of DMSO, 0.13 uL of SYBR Green (1/375 dilution, S7563 Invitrogen), 0.5 µL each of respective forward and reverse primers (2.5 µM) and 1.34 µL of RNAase free water. In indicated experiments, for PCR reaction of 5 µL volume the composition was the same as RT-PCR reaction except 0.2 µL of RNAase free water was added instead of reverse transcriptase. Real time RT-PCR targeting rRNA or tmRNA was performed by reverse transcription at 50° C. for 5 min, inactivation of reverse transcriptase and activation of hotstart DNA polymerase at 97° C. for 5 min, followed by 35 to 40 cycles of cDNA amplification (denaturation at 95° C. for 5 sec, annealing at 63° for 7 sec, and extension at 72° C. for 10 sec) in Eco Real Time PCR system (Illumina) using a double stranded DNA binding fluorescent dye, SYBR Green. Real time RT-PCR or PCR targeting mRNA the following examples was performed by reverse transcription at 42° C. for 20 min, inactivation of reverse transcriptase and activation of hotstart DNA polymerase at 97° C. for 5 min, followed by 35 to 40 cycles of cDNA amplification (denaturation at 95° C. for 3 sec, annealing at 66° for 3 sec, and extension at 72° C. for 15 sec).

Example 1: The Growth of Bacteria in Partially Lysed then Enriched Whole Blood Sample In the following examples, the method to ensure the growth of bacteria in whole blood sample after partial lysis of blood cells and enrichment of the blood culture was described. *Klebsiella pneumoniae* species was used as an example. The blood cells in the *K. pneumoniae* spiked whole blood were partially lysed by a lysing reagent, and most of the supernatant was removed after centrifugation. The remaining minimal volume of the liquid containing harvested microbial cells was enriched with TSB growth medium and pre-incubated at 37° C. to allow the bacteria in the mixture multiply.

*K. pneumoniae* cells were spiked into 2 mL of EDTA-treated whole blood at 100 CFU/mL concentrations. Blood cell lysing reagent of 200 uL, containing 40 mg/mL Saponin, 10 mg/mL SPS and 1% PPG, was added to the blood. The content was thoroughly mixed by inverting followed by vortexing at low speed for 10 sec, centrifugation at 12,000 rpm for 2 min and removal of 1.8 mL of the supernatant, leaving 200 µL of the liquid and the sedimented remaining blood cells and the microbial cells. One wash cycle was performed by adding 1.8 mL of TSB medium to the remaining liquid supernatant of 200 uL, mixing by inverting, centrifugation at 12,000 rpm for 2 min and removal of 1.8 mL of the supernatant, 200 μL of the liquid and the sedimented remaining blood cells and the microbial cells. The remaining minimal volume of the liquid was enriched with 3.8 mL TSB growth medium, mixed thoroughly by inverting and pre-incubated at 37° C. for 2 hr to allow the bacteria in the mixture multiply. At 0, 1 and 2 hr time point of pre-incubation, 1 mL each of the culture was subjected to blood sample pretreatment procedure which includes blood cell lysis step followed by 4 wash cycles was performed as described above.

K. pneumoniae cells in the resulting pretreated sample was lysed by electrical lysis and the cell lysate of 1 uL containing nominal 1 cell was subjected to RT-PCR. The rRNA primers used in this example are rRNA Primer #2 (enterob4) forward (5'-ACAAGCGGTGGAGCATGTGG-3') (SEQ. ID 1) and rRNA Primer #2 (enterob4) reverse (5'-GCGGGACTTAACCCAACATTTCAC-3') (SEQ. ID 2). The 16S rRNA fragments of 166 base pairs were amplified by rRNA primer pair #2. The tmRNA primers used in this example are tmRNA Primer #C forward (5'-GCAAACGACGAAAACTACGCTTTAGC-3') (SEQ. ID 3) and tmRNA Primer #C reverse (5'-CCTA-CATCCTCGGTACTACATGC-3') (SEQ. ID 4). The tmRNA fragments of 240 base pairs (nucleotides 97 to 337 using K. pneumoniae str. Kp52.145 as a reference) were amplified by tmRNA primer pair #C. The real time fluorescence signal versus cycle number is presented in FIG. 3 to show the growth of bacteria in the enriched blood culture.

Example 2: Antimicrobial Sensitivity Testing of Bacteria in Partially Lysed then Enriched Whole Blood Sample In the following examples, the method to perform antimicrobial sensitivity testing of bacteria in whole blood sample after partial lysis of blood cells and enrichment of the blood culture was described. *Klebsiella pneumoniae* species was used as an example. The blood cells in the *K. pneumoniae* spiked whole blood were partially lysed by a lysing reagent, and most of the supernatant was removed after centrifugation. The remaining minimal volume of the liquid was enriched with TSB growth medium and pre-incubated at 37° C. for to allow the bacteria in the mixture multiply. At the end the pre-incubation period, the antimicrobial sensitivity test was performed by aliquoting the culture into multiple tubes, one without antibiotic and the remaining with different antibiotics.

K. pneumoniae cells were spiked into 2 mL of EDTA-treated whole blood at 100 CFU/mL concentrations. Blood cell lysing reagent containing 40 mg/mL Saponin, 10 mg/mL SPS and 1% PPG in water of 200 uL was added to the blood. The content was thoroughly mixed by inverting followed by vortexing at low speed for 10 sec, centrifugation at 12,000 rpm for 2 min and removal of 1.8 mL of the supernatant, leaving 200 μL of the liquid and the sedimented remaining blood cells and the microbial cells. One wash cycle was performed by adding 1.8 mL of TSB medium to the remaining liquid supernatant of 200 uL, mixing by inverting, centrifugation at 12,000 rpm for 2 min and removal of 1.8 mL of the supernatant, 200 μL of the liquid and the sedimented remaining blood cells and the microbial cells. The remaining minimal volume of the liquid was supplemented with 3.8 mL TSB growth medium, mixed thoroughly by inverting and pre-incubated at 37° C. for 2 hours to allow the bacteria in the mixture multiply. At the end the pre-incubation period, 1 mL each of the culture was distributed into multiple tubes. One tube was designated as non-treated growth control tube without any antibiotic, and 8 ug/mL final concentrations of norfloxacin and tetracycline were added to the remaining respective tubes. The culture tubes were incubated at 37° C. for 2 hours and at the end of the incubation time the respective TSB-enriched blood culture of 1 mL was subjected to blood sample pretreatment procedure which includes blood cell lysis step followed by 4 wash cycles was performed as described above. K. pneumoniae cells in the resulting pretreated sample was lysed by electrical lysis and the cell lysate of 1 uL containing nominal 1 cell was subjected to RT-PCR.

The rRNA primers used in this example are rRNA Primer #1 (enterob2) forward (5'-GTGCCCTT-GAGGCGTGGCTTC-3') (SEQ. ID. 5), rRNA Primer #1 (enterob2) reverse (5'-GCGGGACTTAACCGAACATT-CAC-3') (SEQ. ID. 6), rRNA Primer #2 (enterob4) forward (5'-ACAAGCGGTGGAGCATGTGG-3') (SEQ. ID. 7), rRNA Primer #2 (enterob4) reverse (5'-GCGGGACT-TAACCCAACATTTCAC-3') (SEQ. ID. 8), rRNA Primer #3 (ebGN3) forward (5'-ACTTTCAGCGGGGAGGAAGG-3') (SEQ. ID. 9) and rRNA Primer #3 (ebGN3) reverse (5'-GCGGGACTTAACCCAACATTTCAC-3') (SEQ. ID. 10). The 16S rRNA fragments of 203 base pairs (nucleotides 504 to 707 using K. pneumoniae str. Kp52.145 as a reference) were amplified by primer pair #1, 166 base pairs by primer pair #2 and 666 base pairs by primer pair #3.

The tmRNA primers used in this example are tmRNA Primer #A forward (5'-GCAAACGACGAAAAC-TACGCTTTAGC-3') (SEQ. ID 11), tmRNA Primer #A reverse (5'-GCTTAGTCAGTCTTTACATTCGC-3') (SEQ. ID 12), tmRNA Primer #B forward (5'-GCAAACGACGAAAACTACGCTTTAGC-3') (SEQ. ID 13), tmRNA Primer #B reverse (5'-CGGACGGACACGC-CACTAAC-3') (SEQ. ID 14), tmRNA Primer #C forward (5'-GCAAACGACGAAAACTACGCTTTAGC-3') (SEQ. ID 15), tmRNA Primer #C reverse (5'-CCTA-CATCCTCGGTACTACATGC-3') (SEQ. ID 16), tmRNA Primer #D forward (5'-GGGATTTGCGAAACC-CAAGGTGC-3') (SEQ. ID 17), tmRNA Primer #D reverse (5'-GTTTTAACGCTTCAACCCCAGGC-3') (SEQ. ID 18), tmRNA Primer #E forward (5'-GGGATTTGCGAAACC-CAAGGTGC-3') (SEQ. ID 19), tmRNA Primer #E reverse (5'-GCTTAGTCAGTCTTTACATTCGC-3') (SEQ. ID 20), tmRNA Primer #F forward (5'-GGGATTTGCGAAACC-CAAGGTGC-3') (SEQ. ID 21), tmRNA Primer #F reverse (5'-CGGACGGACACGCCACTAAC-3') (SEQ. ID 22), tmRNA Primer #G forward (5'-GGGATTTGCGAAACC-CAAGGTGC-3') (SEQ. ID 23), tmRNA Primer #G reverse (5'-CCTACATCCTCGGTACTACATGC-3') (SEQ. ID 24). The tmRNA fragments of 218 base pairs (nucleotides 97 to 315 using K. pneumoniae str. Kp52.145 as a reference) were amplified by primer pair #A, 183 base pairs by primer pair #B, 240 base pairs by primer pair #C, 221 base pairs by primer pair #D, 293 base pairs by primer pair #E, 258 base pairs by primer pair #F and 315 base pairs by primer pair #G.

Figures 8, 9:
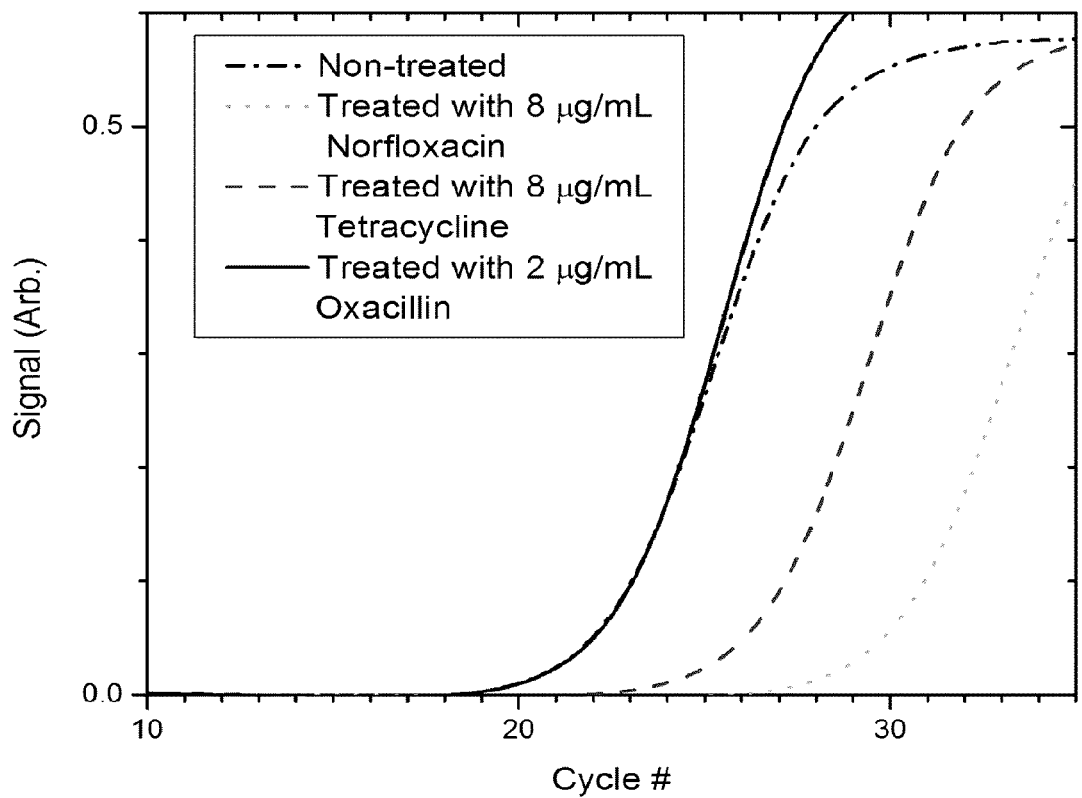
FIG. 8 plots the real time RT-PCR signals of *K. pneumoniae* rRNA detection obtained by processing a whole blood sample, the method involving lysis of blood cells and the addition of growth media, and subsequent pre-incubation for 2 hours, followed by 2 hours of incubation with or without exposure to 8 ug/mL of norfloxacin or tetracycline.
FIG. 9 shows a table of the real time RT-PCR Ct values of *K. pneumoniae* rRNA detection obtained by processing a whole blood sample, the method involving lysis of blood cells and the addition of growth media, and subsequent pre-incubation for 2 hours followed by 2 hours of incubation with or without exposure to 8 ug/mL of norfloxacin or tetracycline.

The real time fluorescence signal versus cycle number is presented in FIGS. 8 and 9 to demonstrate the sensitivity tests using norfloxacin and tetracycline. In this example, the reduction of rRNA and tmRNA in response to the antibiotic was demonstrated compared to without antibiotic (Non-treated) culture.

Example 3: The Probe Dependence of the Specificity by which an mRNA Target is Detected in the Presence of its Corresponding gDNA In the Examples 3 and 4, Gram-negative *E. Coli* cells were grown on LB agar plates and a single colony of cells was cultured in LB broth overnight at 37° C. To perform experiments with cells in exponential growth phase, the overnight culture of 500 uL was inoculated into 5 mL of LB broth and incubated with shaking at 37° C. for indicated duration until the $OD_{600\ nm}$ reached between 0.3 to 0.5, which corresponds to approximately $10^8$ CFU/mL. The cell suspension of 1 mL was centrifuged at 10,000 rpm for 5 min. The cell pellet was washed twice and re-suspended in 1 mL of 0.5 mM phosphate buffer pH 7.4, pre-filtered through a 0.2 μm filter.

The washed cell suspension was 10-fold diluted to approximately $10^7$ CFU/mL and 50 uL of which was incubated at 42° C. for 3 min to induce heat-shock condition. Heat-shocked cells were immediately diluted serially to $10^4$ CFU/mL and subjected to E-lysis.

In the following examples, real-time reverse transcription PCR (RT-PCR) or real-time PCR assay was performed to detect a specific target region in DnaK mRNA or gDNA of *E. coli* respectively. The primers were designed by sequence alignment software (Bioedit, Ibis Biosciences, USA) and primer design software (Primer3, National Institutes of Health). The cell lysate following the electrical lysis was subjected to real-time RT-PCR or PCR. In addition to the sample, pre-filtered phosphate buffer used for cell suspension was subjected to RT-PCR or PCR as a negative control.

Figure 10:
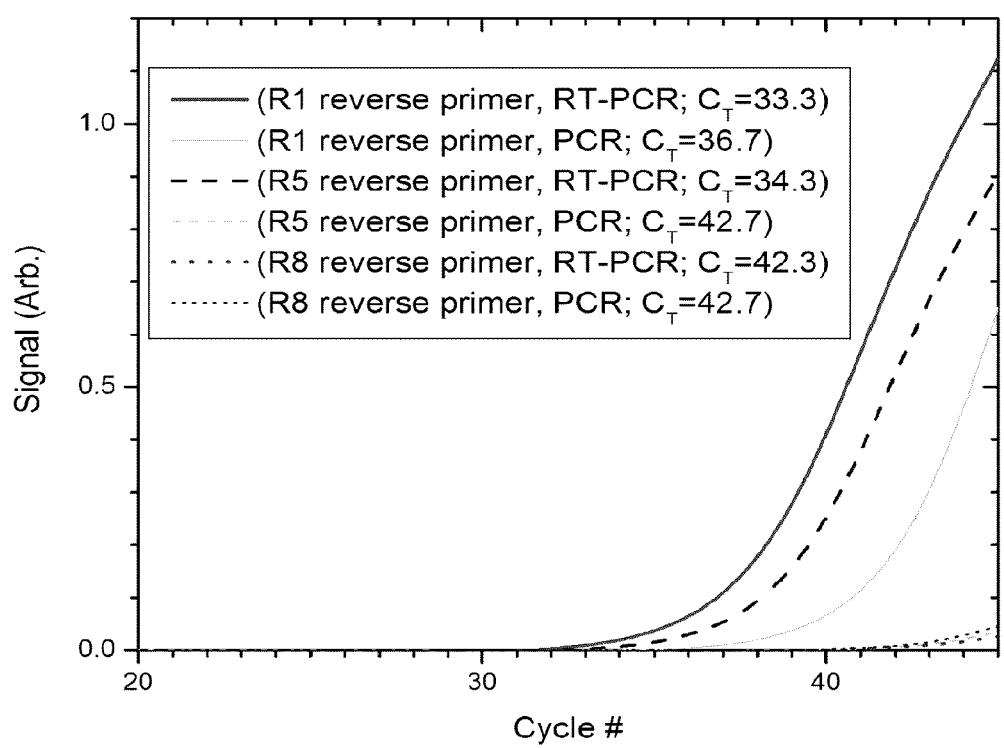
FIG. 10 plots the real-time RT-PCR and PCR signals corresponding to the detection of DnaK mRNA with different probes.

In this example, the overnight *E. coli* culture of 500 uL was inoculated into 5 mL of LB broth and incubated with shaking at 37° C. for 90 min. After washing and re-suspension of the cells in phosphate buffer as described above, the cells were incubated at 42° C. for 3 min to induce the heat-shock immediately before the E-lysis. The cell lysate following the electrical lysis of 1 uL containing nominal 10 cells was subjected to real-time RT-PCR or PCR only. DnaK forward primer (5'-GTACTAC-CAACTCTTGTGTAGCG-3') (SEQ. ID. 25), R1 reverse primer (5'-AGCAGCAATAATTTTGAACGGC-3') (SEQ. ID. 26), R5 reverse primer with 5' tag (SEQ. ID. 27)
(5'-<u>AGTACGCACGG</u>TATCAGCAGCAAT-3')

and R8 reverse primer with (SEQ. ID. 28)
5' tag (5'-<u>GCAGCACGG</u>TTTTGAACGGCAT-3')

were used in this example. The real time fluorescence signal versus cycle number is presented in FIG. 10.

As it is observed, while using untagged reverse primer the difference in the CT values of RT-PCR and RT assays are only 3.4 cycles, the difference is increased to 8.4 cycles. This amounts to a 32 fold improvement in background suppression by an appropriate primer selection. Therefore, the primer sequence influences the amplification and the ratio of amplicons resulting from gDNA to those resulting from mRNA.

Figure 11:
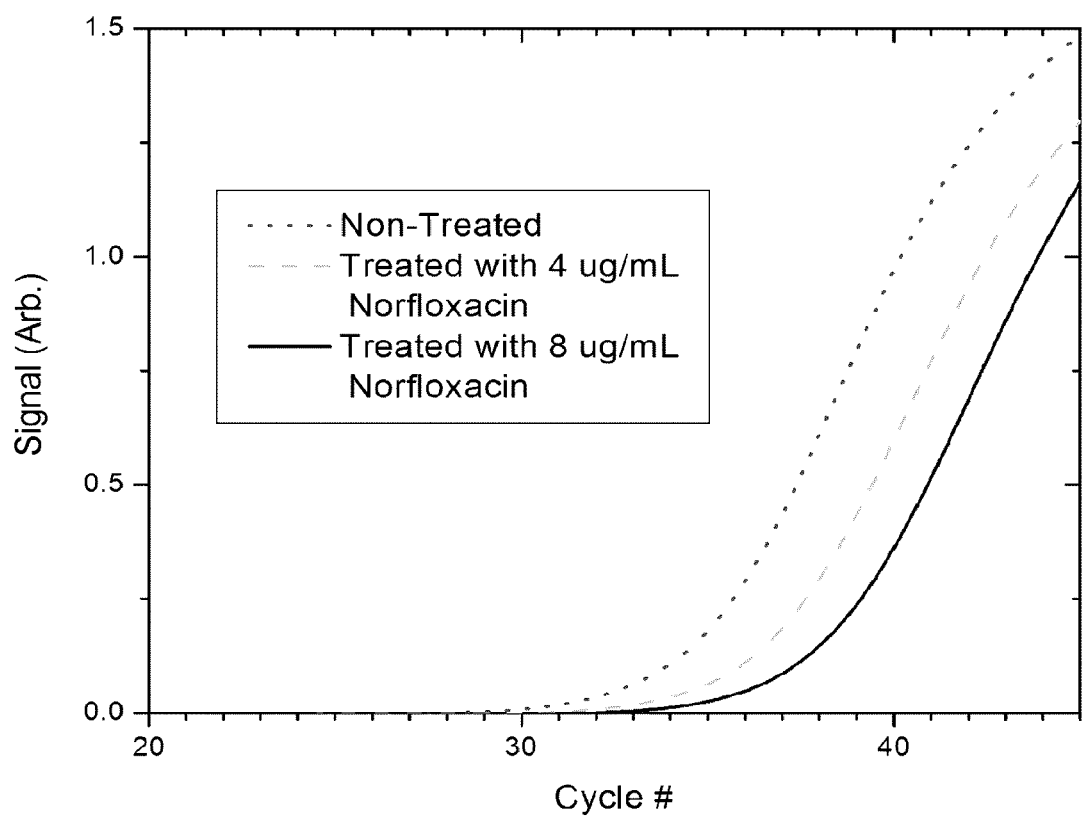
FIG. 11 plots the real time RT-PCR and PCR signals corresponding to microbial cells after two hours of exposure to different doses of an antibiotic.

Example 4: The Difference in mRNA Levels after Exposure of a Bacteria to an Antibiotic In this examples, the overnight *E. coli* culture of 500 uL was inoculated into 5 mL of LB broth with or without antibiotic norfloxacin 4 or 8 ug/mL final concentration and incubated with shaking at 37° C. for 120 min. After washing and re-suspension of the cells in phosphate buffer as described above, the cells were incubated at 42° C. for 3 min to induce the heat-shock immediately before the E-lysis. The cell lysate following the electrical lysis of 1 uL containing nominal 10 cells was subjected to real-time RT-PCR (RT+) or PCR (RT−). DnaK forward primer (5'-GTACTAC-CAACTCTTGTGTAGCG-3') (SEQ. ID. 29) and R5 reverse primer with 5' tag (SEQ. ID 30)
(5'-<u>AGTACGCACGG</u>TATCAGCAGCAAT-3')

were used in this example. The real time fluorescence signal versus cycle number is presented in FIG. 11.

As it is observed, the exposure of microbial cells to the antibiotic norfloxacin reduced the quantity of target mRNA by approximately 8-16 times (corresponding to 3-4 PCR cycles). These results indicate that the mRNA level due to heat induction is substantially affected by susceptibility to the antimicrobial agent.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

We claim:

1. A method of performing rapid antibiotic susceptibility testing, comprising:
   obtaining a first sample and a second sample, wherein the first sample and the second sample are derived from a common subject in the absence of an initial microbial growth step;
   adding growth media to the second sample and pre-incubating the second sample under conditions suitable for promoting microbial growth;
   while pre-incubating the second sample, performing a multiplexed identification test panel on the first sample and identifying a presence of one or more microbial cells with the first sample, wherein the multiplexed identification test panel is performed on the first sample in the absence of culturing the first sample; and
   performing an antimicrobial susceptibility test on the second sample to determine a measure of the effectiveness of an antibiotic on microbial cells within the second sample, wherein the antibiotic is selected based on the results from the multiplexed identification test panel.

2. The method according to claim 1 wherein an antibiotic absorbing agent is added to the second sample prior to pre-incubating the second sample, and wherein the antibiotic absorbing agent is removed from the second sample prior to performing the antimicrobial susceptibility test.

3. The method according to claim 1 wherein a presence of the microbial cells within the first sample is identified among the multiplexed identification test panel within approximately one hour.

4. The method according to claim 1 wherein performing one or both of the multiplexed identification test panel and the antimicrobial susceptibility test comprises performing reverse transcription and subsequent multiplexed amplification to detect rRNA.

5. The method according to claim 1 wherein each test of the multiplexed identification test panel is associated with one of a kingdom, family, Gram status, genus, species and strain.

6. The method according to claim 1 wherein the second sample is obtained from the first sample.

7. The method according to claim 1 wherein the first sample and the second sample are whole blood samples.

8. The method according to claim 1 wherein the first sample and the second sample are derived one of sputum samples, urine samples, cerebral spinal fluid samples.

9. The method according to claim 1 where the first sample and the second sample are one of serum samples and plasma samples.

10. The method according to claim 1 wherein one or more combinations of positive test results from the multiplexed identification test panel has at least one corresponding antibiotic associated therewith, and wherein the at least one selected antibiotic is selected by:
    selecting, as the selected antibiotic, a corresponding antibiotic associated with the results from the multiplexed identification test panel, and wherein the determination of the effectiveness of the selected antibiotic is performed as a reflex test based on the selected antibiotic without receiving input from a medical practitioner.

11. The method according to claim 1 where the antimicrobial susceptibility test is performed by:
    obtaining, from the second sample, at least a primary aliquot and a reference aliquot;
    adding, to the primary aliquot, the selected antibiotic, the selected antibiotic having been selected, at least in part, based on the results of the multiplexed identification test panel;
    incubating the primary aliquot and the reference aliquot under conditions suitable for promoting microbial growth for testing the effectiveness of the selected antibiotic;
    separating microbial cells from the primary aliquot and resuspending the separated microbial cells to obtain a primary suspension;
    separating microbial cells from the reference aliquot and resuspending the separated microbial cells to obtain a reference suspension;
    lysing the microbial cells in the primary suspension and the reference suspension, thereby obtaining a primary lysate and a reference lysate;

performing reverse transcription and amplification on the primary lysate, thereby obtaining a primary assay signal;

performing reverse transcription and amplification on the reference lysate, thereby obtaining a reference assay signal; and comparing the primary assay signal and the reference assay signal to obtain measure of the effectiveness of the selected antibiotic against the microbial cells.

12. The method according to claim 11, wherein the reverse transcription and amplification is performed to detect rRNA, and wherein a decrease in the primary assay signal relative to that of the reference assay signal is indicative of effectiveness of the selected antibiotic.

13. The method according to claim 11, wherein the reverse transcription and amplification is performed to detect tmRNA, and wherein a decrease in the primary assay signal relative to that of the reference assay signal is indicative of effectiveness of the selected antibiotic.

14. The method according to claim 11, wherein the reverse transcription and amplification is performed to detect mRNA, and wherein a change in the primary assay signal relative to that of the reference assay signal is employed to determine the effectiveness of the selected antibiotic.

15. The method according to claim 14 further comprising subjecting the primary aliquot and the reference aliquot to a stimulus configured to induce the production of mRNA, wherein the stimulus is selected such that the production of mRNA for susceptible and/or resistant microbial cells is altered due to exposure of the microbial cells to the antibiotic.

16. The method according to claim 11 wherein the reverse transcription and amplification detects a plurality of nucleic acid sequences, such that the plurality of nucleic acid sequences include nucleic acid sequences associated with microbial cell types that are members of the multiplexed identification test panel.

17. The method according to claim 11 wherein the reverse transcription and amplification detects at least one nucleic acid sequence that is conserved among two or more types of microbial cells that are members of the multiplexed identification test panel.

18. The method according to claim 11 wherein the microbial cells are separated by centrifugation or filtration.

19. The method according to claim 11 wherein the primary aliquot and the reference aliquot are incubated, under conditions suitable for promoting microbial growth, prior to adding the selected antibiotic to the primary aliquot.

20. The method according to claim 11 wherein the primary aliquot is a first primary aliquot and the selected antibiotic is a first selected antibiotic, and wherein one or more additional aliquots are obtained from the second sample, the method further comprising adding, to each additional aliquot, an additional selected antibiotic and processing each additional aliquot to obtain a measure of the effectiveness of each additional selected antibiotic against the microbial cells, wherein each additional selected antibiotic is selected, at least in part, based on the identification of the microbial cells.

* * * * *